(12) United States Patent
Dantus et al.

(10) Patent No.: US 10,267,739 B2
(45) Date of Patent: Apr. 23, 2019

(54) LASER SYSTEM FOR STANDOFF DETECTION

(71) Applicant: Board of Trustees of Michigan State University, East Lansing, MI (US)

(72) Inventors: Marcos Dantus, Okemos, MI (US); Marshall Thomas Bremer, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 353 days.

(21) Appl. No.: 14/907,992

(22) PCT Filed: Jul. 31, 2014

(86) PCT No.: PCT/US2014/049117
§ 371 (c)(1),
(2) Date: Jan. 27, 2016

(87) PCT Pub. No.: WO2015/060921
PCT Pub. Date: Apr. 30, 2015

(65) Prior Publication Data
US 2016/0169806 A1    Jun. 16, 2016

Related U.S. Application Data

(60) Provisional application No. 61/861,833, filed on Aug. 2, 2013.

(51) Int. Cl.
*G01N 21/65* (2006.01)
*G01J 3/44* (2006.01)
(Continued)

(52) U.S. Cl.
CPC ............... *G01N 21/65* (2013.01); *G01J 3/36* (2013.01); *G01J 3/44* (2013.01); *G01N 33/227* (2013.01);
(Continued)

(58) Field of Classification Search
CPC ......... G01N 21/65; G01N 33/227; G01J 3/44; G01J 3/36
See application file for complete search history.

(56) References Cited

U.S. PATENT DOCUMENTS 6,108,081 A    8/2000 Holtom et al.
7,105,811 B2   9/2006 Dantus et al.
(Continued)

FOREIGN PATENT DOCUMENTS

| EP | 2157415 A1 | 2/2010 | |
|---|---|---|---|
| EP | 2806263 A2 * | 5/2013 | ............. G01N 21/65 |
| WO | WO-2010/007630 A1 | 1/2010 | |

OTHER PUBLICATIONS

Bremer, Marshall T., et al.; "Highly Selective Standoff Detection and Imaging of Trace Chemicals in a Complex Background using Single-Beam Coherent Anti-Stokes Raman Spectroscopy", Applied Physics Letters, Sep. 9, 2011, four pages.
(Continued)

*Primary Examiner* — Kara E. Geisel
(74) *Attorney, Agent, or Firm* — Harness, Dickey & Pierce, PLC

(57) ABSTRACT

A laser system and method employing stimulated Raman scattering using a main laser pulse and a delayed replica reference pulse are provided. A further aspect calculates stimulated Raman loss and stimulated Raman gain from a reflected laser light scatter collected from a fabric or paper specimen. In another aspect, a laser system receives a low energy portion of a spectrum of main and reference laser pulses with a first photodetector, receives a higher energy portion of the spectrum of the main and reference pulses with a second photodetector, and uses a controller to determine a Raman active phonon transfer of energy manifested as an increase in the reflected laser scatter in a lower energy portion of the spectrum and a decrease in a higher energy
(Continued)

portion of the spectrum. In yet another aspect, the controller automatically determines if a hazardous particle or substance such as an explosive, is present on a specimen.

30 Claims, 19 Drawing Sheets

(51) Int. Cl.
*G01J 3/36* (2006.01)
*G01N 33/22* (2006.01)
*G01J 3/02* (2006.01)

(52) U.S. Cl.
CPC ... *G01J 3/0224* (2013.01); *G01N 2201/06113* (2013.01)

(56) References Cited

U.S. PATENT DOCUMENTS

| | | | |
|---|---|---|---|
| 7,256,885 B2 | 8/2007 | Silberberg et al. | |
| 7,352,458 B2 | 4/2008 | Xie et al. | |
| 7,388,668 B2 | 6/2008 | Potma et al. | |
| 7,403,282 B2 | 7/2008 | Silberberg et al. | |
| 7,414,729 B2 | 8/2008 | Xie et al. | |
| 7,439,497 B2 | 10/2008 | Dantus et al. | |
| 7,450,618 B2 | 11/2008 | Dantus et al. | |
| 7,542,137 B2 | 6/2009 | Murugkar et al. | |
| 7,567,596 B2 | 7/2009 | Dantus et al. | |
| 7,583,710 B2 | 9/2009 | Dantus et al. | |
| 7,609,731 B2 | 10/2009 | Dantus et al. | |
| 7,616,304 B2 | 11/2009 | Gankkhanov et al. | |
| 7,826,051 B2 | 11/2010 | Silberberg et al. | |
| 7,973,936 B2 | 7/2011 | Dantus | |
| 8,027,032 B2 | 9/2011 | Xie et al. | |
| 8,208,504 B2 | 6/2012 | Dantus et al. | |
| 8,208,505 B2 | 6/2012 | Dantus et al. | |
| 8,265,110 B2 | 9/2012 | Dantus et al. | |
| 8,300,669 B2 | 10/2012 | Dantus et al. | |
| 8,311,069 B2 | 11/2012 | Dantus et al. | |
| 8,618,470 B2 | 12/2013 | Dantus et al. | |
| 8,630,322 B2 | 1/2014 | Dantus et al. | |
| 8,633,437 B2 | 1/2014 | Dantus et al. | |
| 8,675,699 B2 | 3/2014 | Dantus et al. | |
| 8,861,075 B2 | 10/2014 | Dantus et al. | |
| 9,018,562 B2 | 4/2015 | Dantus | |
| 9,048,632 B1 | 6/2015 | Dantus et al. | |
| 9,202,678 B2 | 12/2015 | Dantus et al. | |
| 2003/0099264 A1 | 5/2003 | Dantus et al. | |
| 2004/0089804 A1 | 5/2004 | Dantus et al. | |
| 2004/0233944 A1 | 11/2004 | Dantus et al. | |
| 2005/0021243 A1 | 1/2005 | Dantus et al. | |
| 2005/0232317 A1 | 10/2005 | Dantus et al. | |
| 2006/0056468 A1 | 3/2006 | Dantus et al. | |
| 2006/0066848 A1 | 3/2006 | Frankel | |
| 2006/0187974 A1 | 8/2006 | Dantus | |
| 2008/0170218 A1 | 7/2008 | Dantus et al. | |
| 2008/0309931 A1 | 12/2008 | Silberberg et al. | |
| 2009/0122819 A1 | 5/2009 | Dantus et al. | |
| 2009/0188901 A1 | 7/2009 | Dantus | |
| 2009/0207869 A1 | 8/2009 | Dantus et al. | |
| 2009/0216299 A1 | 8/2009 | Dantus | |
| 2009/0238222 A1 | 9/2009 | Dantus et al. | |
| 2009/0256071 A1 | 10/2009 | Dantus et al. | |
| 2009/0257464 A1 | 10/2009 | Dantus et al. | |
| 2009/0296744 A1 | 12/2009 | Dantus et al. | |
| 2010/0123075 A1 | 5/2010 | Dantus et al. | |
| 2010/0187208 A1 | 7/2010 | Dantus et al. | |
| 2010/0208252 A1* | 8/2010 | Marks | G01J 3/10 356/301 |
| 2011/0211600 A1 | 9/2011 | Dantus et al. | |
| 2012/0076504 A1 | 3/2012 | Dantus et al. | |
| 2012/0147911 A1 | 6/2012 | Dantus et al. | |
| 2012/0162641 A1* | 6/2012 | Schmidt | G01J 3/28 356/301 |
| 2013/0127980 A1 | 5/2013 | Haddick et al. | |
| 2013/0162994 A1 | 6/2013 | Xie et al. | |
| 2014/0058367 A1 | 2/2014 | Dantus | |
| 2015/0157209 A1 | 6/2015 | Dantus | |

OTHER PUBLICATIONS

Dudovich, Nirit, et al.; "Single-pulse coherently controlled nonlinear Raman spectroscopy and microscopy", Nature, vol. 418, Aug. 2002, pp. 512-514.

Freudiger, Christian W., et al.; "Label-Free Biomedical Imaging with High Sensitivity by Stimulated Raman Scattering Microscopy", Science, vol. 322, Dec. 19, 2008, pp. 1857-1861.

Fu, Dan, et al.; "Hyperspectral Imaging with Stimulated Raman Scattering by Chirped Femtosecond Lasers", The Journal of Physical Chemistry B, 2013, vol. 117, pp. 4634-4640.

Ll, Haowen, et al.; "Coherent mode-selective Raman excitation towards standoff detection", Optics Express, vol. 16, No. 8, Apr. 14, 2008, pp. 5499-5504.

Labroille, Guillaume, et al.; "Dispersion-based pulse shaping for multiplexed two-photon fluorescence microscopy", Optics Letters, vol. 35, No. 20, Oct. 15, 2010, pp. 3444-3446.

Nose, Keisuke, et al.; "Sensitivity enhancement of fiber-laser-based stimulated Raman scattering microscopy by collinear balanced detection technique", Optics Express, vol. 20, No. 13, Jun. 18, 2012, pp. 13958-13965.

Wang, Ke, et al.; "Advanced Fiber Soliton Sources for Nonlinear Deep Tissue Imaging Biophotonics", IEEE Journal of Selected Topics in Quantum Electronics, vol. 20, No. 2, Mar./Apr. 2014, eleven pages.

Weiner, A. M., et al.; "Femtosecond Pulse Sequences Used for Optical Manipulation of Molecular Motion", Reports, Mar. 16, 1990, pp. 1317-1319.

Woodbury, E. and NG, W., "Correspondence", Proceedings of the IRE 50, No. 11, 1962, pp. 2365-2383.

* cited by examiner

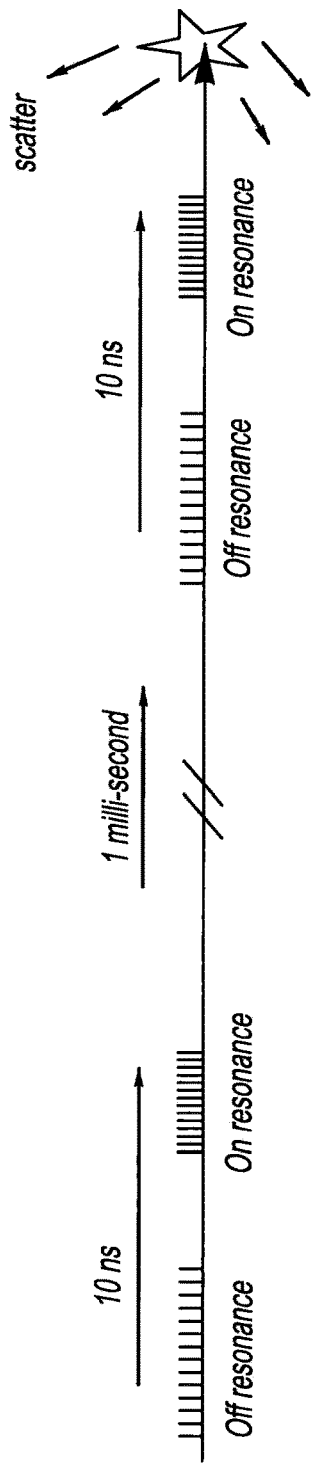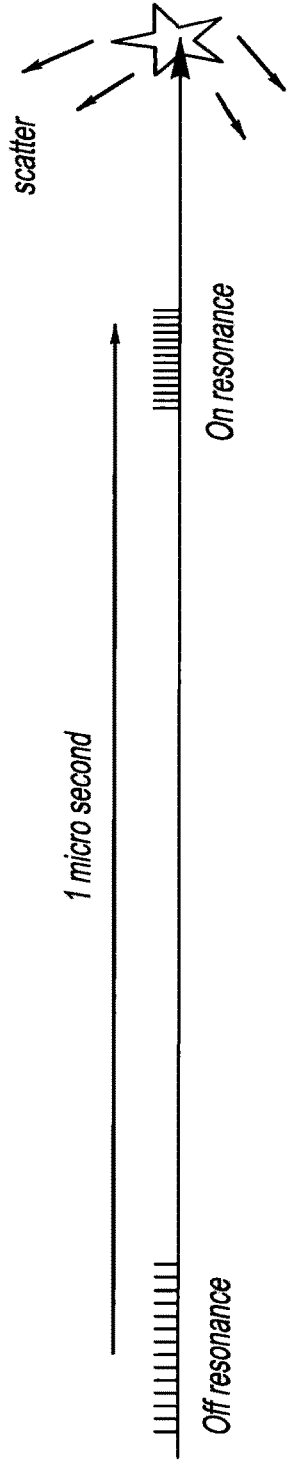
FIG-21
FIG-22

LASER SYSTEM FOR STANDOFF DETECTION

CROSS-REFERENCE TO RELATED APPLICATIONS

This application is a 371 National Phase application of PCT/US2014/049117, filed on Jul. 31, 2014, which claims the benefit of U.S. Provisional Application No. 61/861,833, filed on Aug. 2, 2013, both of which are incorporated by reference herein.

GOVERNMENT RIGHTS

This invention was made with government support under contract no. HSHQDC-09-C-00135 awarded by the U.S. Department of Homeland Security. The government has certain rights in the invention.

BACKGROUND AND SUMMARY

This invention relates generally to a laser system and more particularly to a laser system for standoff detection of hazardous particles on a specimen.

Standoff detection of hazardous materials remains an important challenge. It has been difficult to accurately detect trace quantities of explosives in a non-destructive manner in a public space containing many background chemicals. Non-linear Raman spectroscopy in the form of coherent anti-Stokes Raman scattering ("CARS") has been tried for enhancing the signal of spontaneous Raman emissions through coherent signal addition. A CARS experiment is disclosed in H. Li, D. Harris, B. Xu, P. Wrzesinski, V. Lozovoy and M. Dantus, "Coherent Mode-Selective Raman Excitation Towards Standoff Detection," Optics Express 5499, Vol. 16, No. 8, (Apr. 14, 2008). The analyte, however, was deposited on an ideal and highly reflective polymeric surface, which would not be present for most real-world situations where scanned passengers are wearing clothing made of natural or synthetic fibers (collectively, fabric) or leather, and luggage is made of plastic, fabric or paper-cardboard, which significantly diffuse or absorb the reflective light.

Other Raman-based techniques are disclosed in U.S. Patent Publication No. 2013/0162994 entitled "Systems and Methods Providing Efficient Detection of Back-Scattered Illumination in Modulation Transfer Microscopy or Micro-Spectroscopy," published to Xie et al. on Jun. 27, 2013, U.S. Pat. No. 7,826,051 entitled "Coherently Controlled Nonlinear Raman Spectroscopy," which issued to Silberberg et al. on Nov. 2, 2010, and U.S. Patent Publication No. 2008/0170218 entitled "Ultra-Fast Laser System," which published to Dantus et al. on Jul. 17, 2008, all of which are incorporated by reference herein. It is noteworthy, however, that these prior patent references employ separate pump and anti-Stokes laser pulses. Furthermore, it is noteworthy that paragraph no. 0049 of the Xie patent publication highlights the differences of stimulated Raman scattering ("SRS") microscopy over the CARS approach of the Silberberg patent.

In accordance with the present invention, a laser system and method employ stimulated Raman scattering using a single main laser pulse and a delayed replica reference pulse. A further aspect calculates stimulated Raman loss and stimulated Raman gain from a reflected laser light scatter collected from the surface of common objects such as fabric or paper. In another aspect, a laser system receives a low energy portion of a spectrum of main and reference laser pulses with a first photodetector, receives a higher energy portion of the spectrum of the main and reference pulses with either the first photodetector or with an additional second photodetector, and uses a controller to determine a Raman active phonon transfer of energy manifested as an increase in the reflected laser scatter in a lower energy portion of the spectrum and/or a decrease in a higher energy portion of the spectrum. In yet another aspect, the controller automatically determines if a hazardous particle or substance, such as an explosive, is present on a specimen within three seconds and using a pulse energy greater than 10 nanoJoules. A further aspect uses a laser system on a specimen located at least 0.5 meter away from a transportation security checkpoint structure to which a laser and photodetector are mounted. In still another aspect, a reference laser pulse has a different vibrational selectivity from a main laser pulse, yet the energies and spectra of the main and reference pulses are essentially identical. Software operating a laser system is provided which can calculate stimulated Raman loss and stimulated Raman gain from collected reflected scattered light, while minimizing distortions and background noise, to determine if a harmful substance is present on a light diffusing and/or absorbing specimen.

The laser system and method of the present invention are advantageous over prior devices. For example, the present method and system are capable of identifying small trace particles of hazardous substances on a light scattering and/or absorbing specimen such as fabric or paper. Another advantage is that the present laser system, method and software can scan large areas greater than 0.3×0.3 meters with results determined very quickly. The present system is also advantageous in being able to at least initially identify the hazardous particle on the light diffusing/absorbing specimen with a single laser pulse emission (which is subsequently replicated into an additional reference pulse). Furthermore, another advantage is the low energy required to operate the present system and method, which prevent undesired ablation or destruction of the hazardous substance on the specimen. It is also noteworthy that the present system and method employ SRS, thereby detecting by monitoring changes in an incident laser spectrum, which is different than CARS which detects at new frequencies and uses a narrow band probe pulse. In other words, the present system does not employ CARS and does not employ Raman spectroscopy, therefore it needs no spectrometer. It also noteworthy that the present system and method are advantageously capable of measuring changes in either half or all of the reflected light spectrum, including stimulated Raman loss or stimulated Raman gain, unlike the Xie construction which cannot measure both. Additional advantages and features of the present system will become apparent from the following description and claims, as well as the appended drawings.

BRIEF DESCRIPTION OF THE DRAWINGS

FIGS. 21 and 22 are diagrams illustrating the SRS operation employed in different configurations of the present laser system.

DETAILED DESCRIPTION

Figure 1:
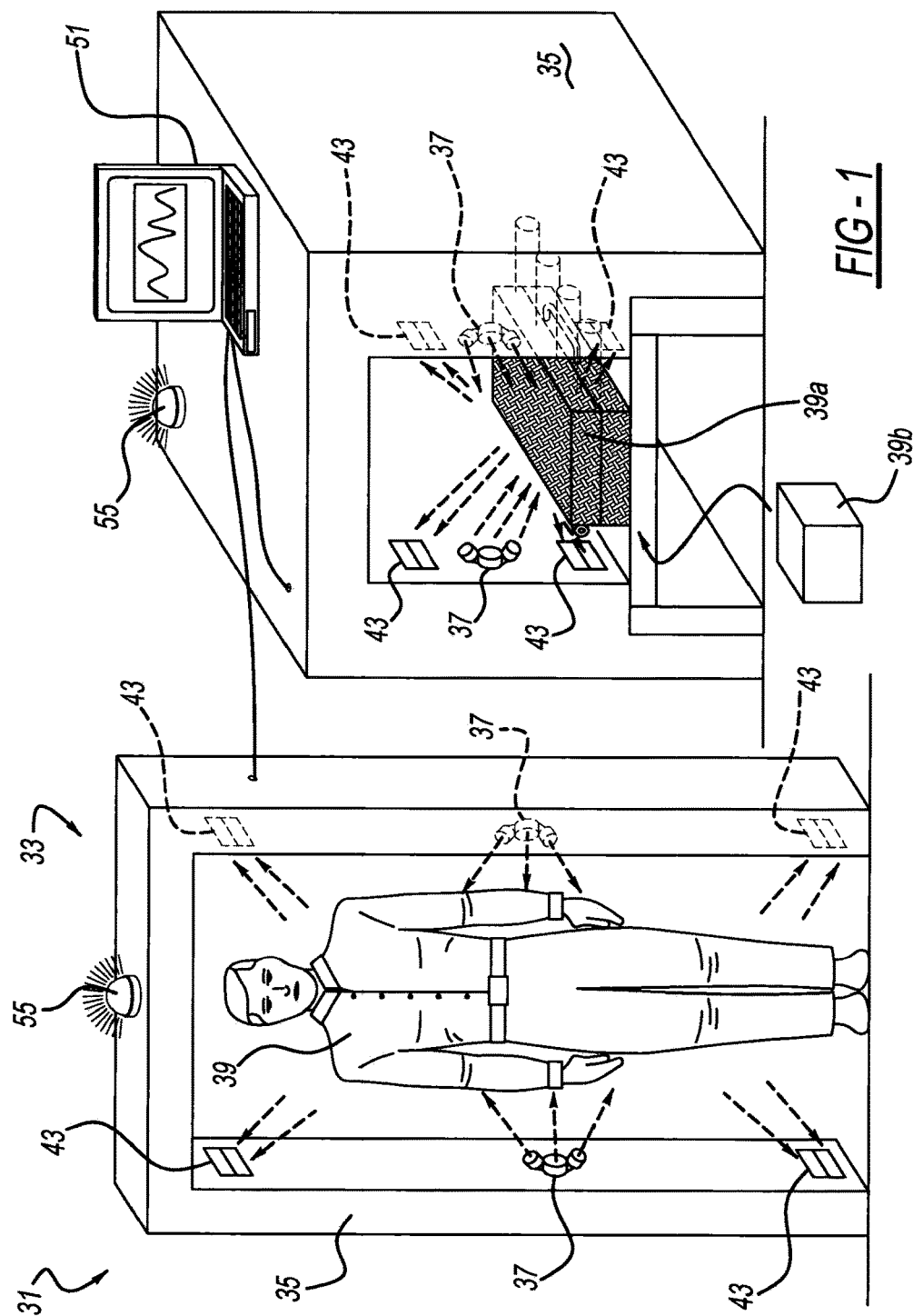
FIG. 1 is a diagrammatic perspective view showing the present laser system employed in transportation security scanning structures.
Figure 2:
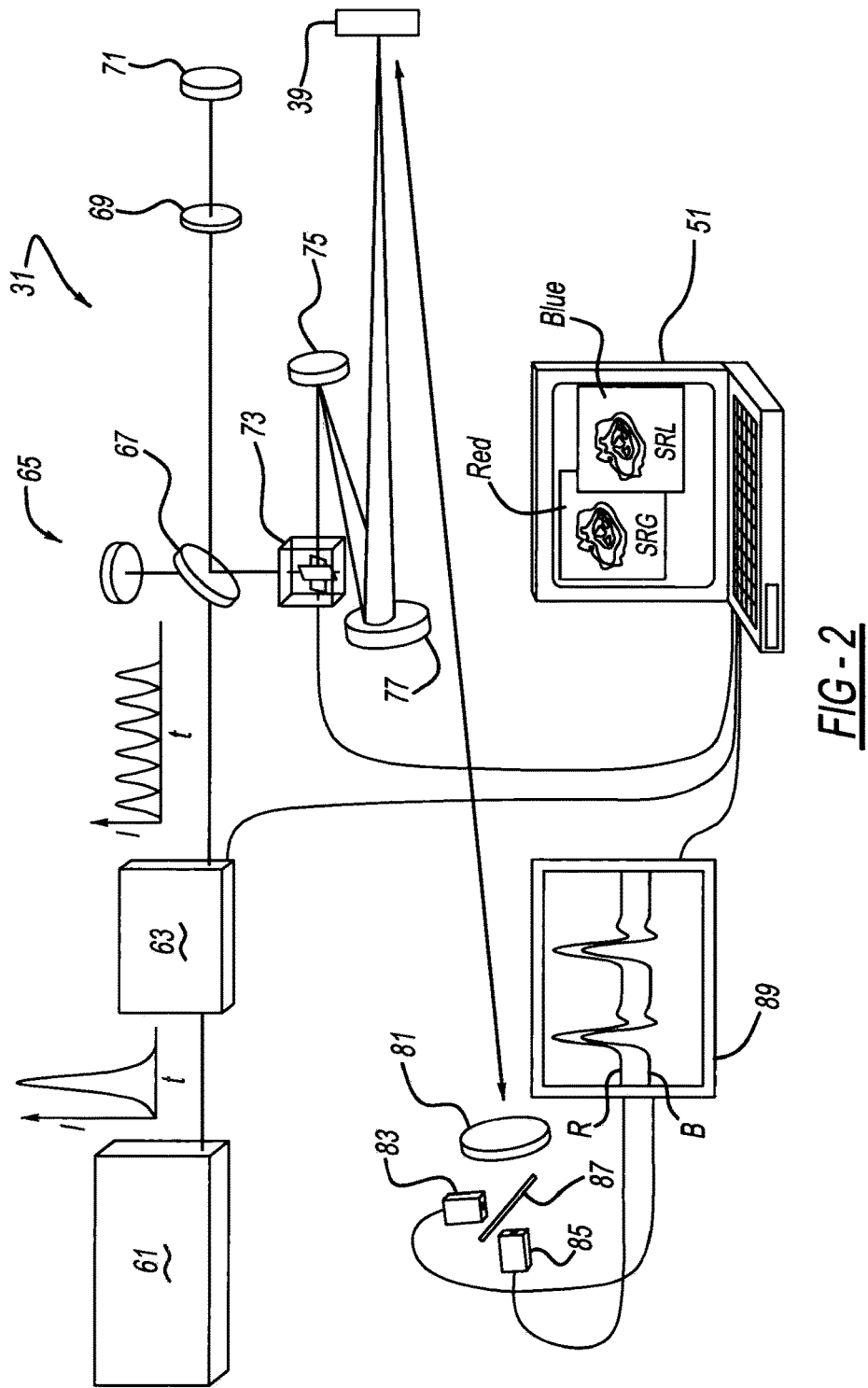
FIG. 2 is a diagrammatic view showing the present laser system for a laboratory setup.
Figure 3:
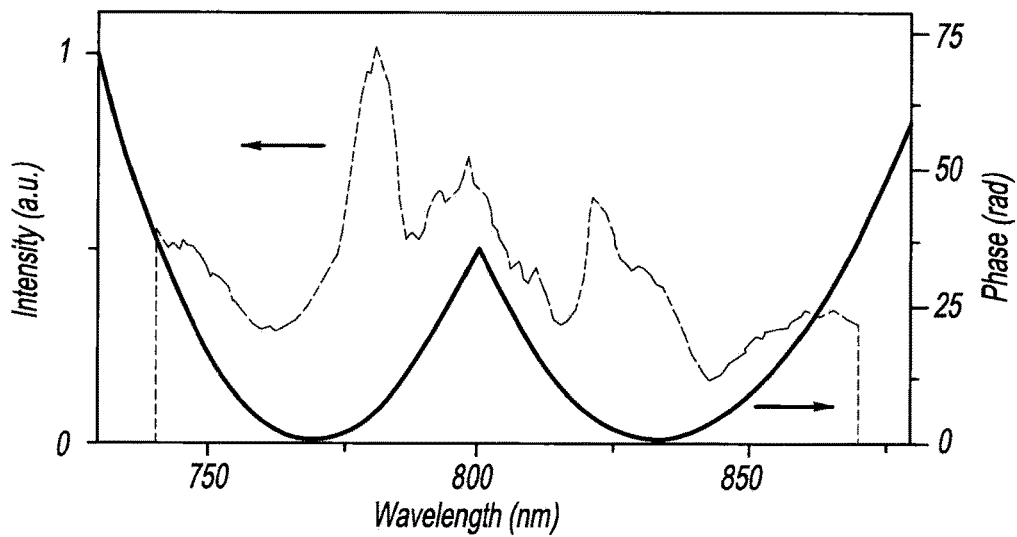
FIG. 3 is a graph showing expected laser spectrum and phase results using the present laser system.

FIG. 1 illustrates a laser system 31 employed in a security checkpoint 33 at a transportation facility, such as an airport, train station or the like. A laser is mounted to each side of a pass through, security scanning structure 35. An optical outlet 37 associated with each laser, is moveably mounted to security structure 35 on either side of a human specimen 39 or luggage specimen 41 or an internal mirror is quickly oscillated by an electromagnetic actuator to vary the output laser beam directions. Sets of photodetectors 43 are also mounted to side surfaces inside security structure 35. A programmable computer controller 51, having a keyboard input, a display screen output, a microprocessor and non-transient memory (for example, a memory micro-chip, ROM, RAM, a disc, a removable memory stick, or the like) for storing and operating programmed software instructions therein, is connected to security scanning structures 35 for sending and receiving electrical signals to and from the laser system, including the photodetectors, as well as warning lights 55 and audible alarms coupled thereto; or the alarm may simply be displayed as a flashing red screen on the display output of the computer.

Laser system 31 provides standoff detection imaging of explosive traces by selective stimulated Raman scattering. Selected excitation of a particular Raman transition is detected by measuring the diffusely scattered laser light from a distant surface, such as a fabric clothing specimen 39 for a person or fabric covering of a luggage specimen 39a or a paper-based cardboard parcel specimen 39b. Unlike in CARS which requires a reflective specimen surface due to directed signals, SRS detects scattering so reflective specimen surfaces are not needed for proper performance. Thus, the present system is ideally suited for use on natural or synthetic fabrics, including cotton, silk, polyester and nylon, as well as leather, plastic and paper surfaces of the clothing or luggage specimens. Laser system 31 preferably simultaneously measures stimulated Raman loss and gain within a single laser shot (in other words, separate pump and probe anti-Stokes Raman laser pulses are not required) and the system is insensitive to the texture, reflectivity and absorptivity optical properties of the specimen surface. The present system therefore detects a transfer of energy occurring when a Raman active mode couples multiple laser frequencies from the original pulse but not the replica pulse, through stimulated Raman scattering at the specimen using only the pulses having a broad bandwidth and without sharp spectral features.

A train of pulses, for example 10-50 subpulses, is created from each emitted main pulse at the frequency of a Raman transition. As will be discussed in more detail hereinafter, this could be accomplished by a pulse shaper or by using a pair of birefringent wedges make two pulses separated by less than one picosecond. These two pulses later become a train of pulses when dispersion is added (such as when linearly chirped). Thus, the present laser system and method are ideally suited to maximize both specificity and sensitivity by detecting an imaging nanogram of analyte microcrystals on paper, fabric, plastic and other substrates at standoff distances of between 0.5 to 10 m (such as from the laser output 37 to specimen 39, using 0.01-1.0 Watt of laser power or 10-1,000 nJ of pulse energy with a pulsed laser having a repetition rate greater than 1 kHz, from a single laser pulse within 3 seconds from the initial laser emission and more preferably within 3 ms.

Stimulated Raman scattering ("SRS") can be described as a third-order wave coupling process mediated by Raman transitions. Phenomenologically, when a ground state molecule is in the presence of two strong fields, there is a transfer of photons from a high-frequency field to a low-frequency field if the frequency differences match a Raman transition within a molecule. Conservation of energy is ensured by changes in the population of the excited vibrational state. The present system employs a single femtosecond laser and computer-controlled pulse shaper to selectively excite a particular vibration, such as that for an explosive particle desired for detection, through the SRS process. The present system and method create an intrinsic reference replicable pulse, delayed in time, from a main pulse which provides optimal measurement of stimulated Raman loss ("SRL") and stimulated Raman gain ("SRG") at low repetition rates, even under single-shot operation. The reference pulse has the same spectrum and energy intensity as the primary pulse but the reference pulse has its phase detuned, thereby allowing simultaneous measurement of SRL and SRG.

FIG. 1 shows a laboratory setup for the present laser system 31. A laser 61 preferably includes a Mira® brand oscillator from Coherent Inc. which emits a sequence or train of 500 femtosecond or less, and more preferably 20 fs or less duration laser pulses which are then shaped by a 4f reflective pulse shaper 63, which is preferably an active computer-controlled 128-pixel phase-only, programmable liquid crystal spatial light modulator ("SLM") which can be obtained from CRi Corp. The shaped series of pulses are then amplified by a regenerative amplifier, for example, a Legend USP brand amplifier from Coherent Inc. Optical continuum generation is obtained when high-order dispersion and other photonic distortions are eliminated by the pulse shaper using multi-photon intrapulse interference phase scan procedures and software which can be obtained by Biophotonic Solutions Inc. Linear chirp is also added. Thereafter, the calculated phase is applied to each pulse by shaper 63. In this setup, a Michelson interferometer 65 creates two co-linear pulses from each main pulse; a beam splitter 67, optical window 69 and mirror 71 are employed in this regard. Window 69 adds dispersion to the replicated reference pulse. The main and replicated pulses are then steered by fast scanning mirrors 73, so they are expanded and focused with the assistance of mirrors 75 and 77. This focuses the main and replica pulses onto the fabric or paper surface of specimen 39.

A lens 81 collects the diffusely reflected scattered light from specimen 39 at a distance greater than 0.5 m and more preferably between 0.5-50 m. The collected and detected signal is split between two fast photodetectors, more preferably photodiodes 83 and 85, using a dichroic mirror 87 therebetween, with the output signal being digitized. The photodetectors will receive and identify the collected diffuse laser scatter by the time of arrival and/or modulation frequency of the relative intensities of the main and reference pulses. The focused laser spot size is 5-1,000 microns and more preferably 50-100 microns.

If a compound of interest, such as an explosive particle (for example, 100 ng of micro-crystalline ammonium nitrate, trinitrotoluene or the like) is within at least 1 cm² area on the cotton or synthetic fabric or paper surface of specimen 39, there will be a transfer of photons between the two halves of the spectrum of the first pulse leading to SRG and SRL. However, this transfer does not happen for the second reference pulse because it has a different phase that tunes it out of resonance. After laser scatter is collected by the photodiodes, the relevant intensity of the two spectral halves of each pulse is recorded with 1 GHZ amplified photodiodes 83 and 85, and digitized with a digitizer 89, such as a Waverunner® 610zi oscilloscope which can be obtained from Teledyne Lecroy, Inc. Alternately, the data is digitized using a ATS9360-1.8 GS/s, 12 bit PCIe Gen2 Digitizer. The computer controller automatically runs the programmed software instructions, to calculate the SRL and SRG. It is noteworthy that the reference replicated pulse is desired to prevent visual features such as brightness, darkness and reflectivity in the substrate from contributing to the processed signal. Furthermore, this method effectively eliminates contributions from laser power fluctuations that otherwise limit the sensitivity of the technique. The combination of selectivity and intrinsic reference, in a robust of detecting and determining of trace quantities of explosives are present on common light scattering and absorbing surfaces in a chemically complex background environment.

Figure 6:
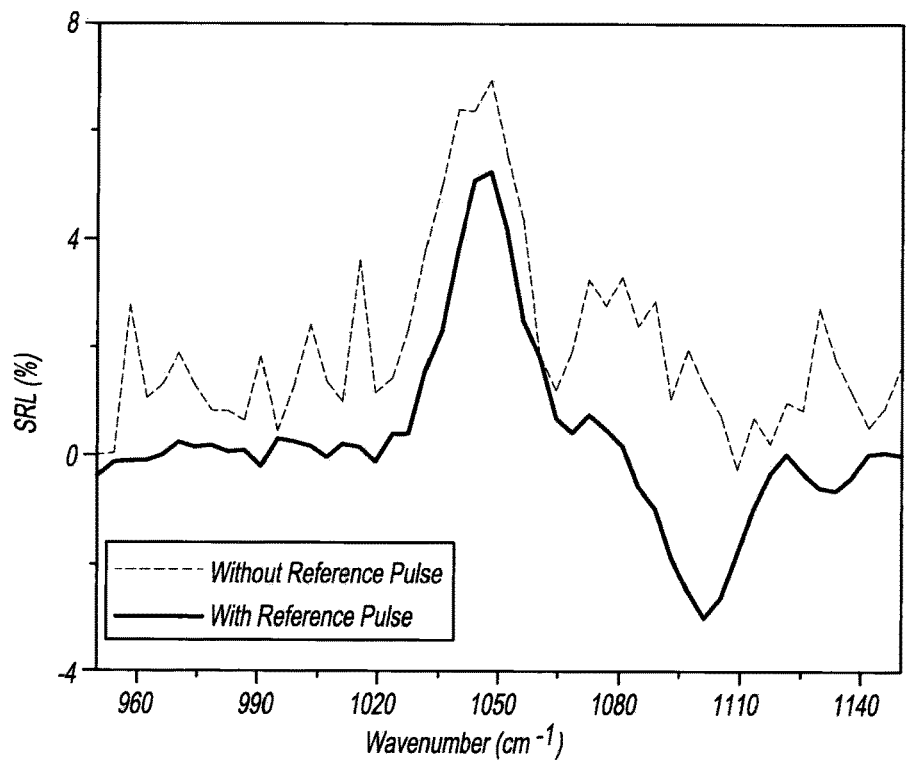
FIG. 6 is a graph showing an expected stimulated Raman loss spectra using the present laser system.

Referring to FIGS. 3-6, the present laser system and method include a noise suppression feature. Measuring SRS requires a reference, since the signal is found in small changes in the laser intensity. Generally, SRS microscopy utilizes lock-in detection and modulation at high frequency, up to half the laser repetition rate. This is effective since laser noise is generally low at small time scales. With amplified, low repetition rate lasers, the shot-to-shot fluctuations are much more significant, generally on the order of 1% or more, which can overwhelm the SRS signal. To compensate for this without extensive averaging, a time-delayed replica of every pulse is created. A small change in the temporal shape, caused by dispersion, of the replicated pulse shifts the excitation frequency and allows the photodetectors and controller to detect SRS by comparing the intensity of the otherwise identical pulses. A related self-referencing technique is implemented for two color SRS microscopy with lock-in detection. There, a delay line effectively doubled the repetition rate of one of the lasers, dramatically reducing the noise at the detection frequency and allowing SRS microscopy with a noisy fiber laser system. FIG. 6 demonstrates the expected effectiveness of this referencing technique where, for the dashed curve, the initial intensity is used as a reference to measure SRL, and the use of the time multiplexed replica pulse is expected to dramatically reduce the noise level as shown in the solid line curve detect SRS by comparing the intensity of the otherwise identical pulses.

Four-wave mixing processes are described in terms of the third order susceptibility, calculated by perturbative expansion of the density matrix. This approach can be modified to describe broadband SRS signals. Following this treatment, the transition amplitude, limited to lowest order (two photon) contributions, from the molecule's ground state to the vibrational state of interest includes an integral of every possible pathway present within the laser bandwidth $$T_{ba}(\Omega) = \frac{1}{2\pi\hbar} \int d\omega \left[ \sum_c \frac{\mu_{bc}\mu_{ac}}{\omega - \omega_{ca} + i\eta} \right] E(\omega) E^*(\omega - \Omega)$$

where $\Omega = \omega_{ba}$ is the Raman transition frequency, c represents the various intermediate electronic states, η is an infinitesimal positive number, and $E(\omega)$ is the Fourier transform of the time domain field. The probability of transition is proportional to the modulus square of this transition amplitude, and contains interference terms between the different pathways. Considering only one electronic state and writing the spectral phase of the field explicitly, $$P_{a \to b} = \frac{1}{4\pi^2\hbar^4} |\mu_{cb}|^2 |\mu_{ca}|^2 \left| \int d\omega \frac{|E(\omega)||E^*(\omega-\Omega)|}{\omega - \omega_{ca} + i\eta} e^{i[\phi(\omega) - \phi(\omega-\Omega)]} \right|^2.$$

This probability is maximized when the accumulated phase, $\phi(\omega) - \phi(\omega-\Omega)$, of every two photon pathway for this transition is identical. The probability approaches zero if this phase varies rapidly and uniformly. This formula (2), with the denominator approximated as a constant, is used to simulate the excitation efficiency for a particular phase and amplitude in FIG. 4.

Detection of the transition is performed by measuring the change in intensity of the laser fields. Measurement of any particular frequency may include contributions from parametric or other non-linear processes, but the sum or difference of signals from different fields allows the controller to isolate the quantity of interest and measure the transition described in equation (2). Summing the intensity of either half of the spectrum eliminates the Raman like parametric processes. One distinguishing benefit in this broadband method is that SRL and SRG are collected simultaneously, providing a method to eliminate electronic processes such as two photon absorption.

The present laser system and method measure stimulated Raman scattering spectra by scanning the applied phase using a computer controlled SLM in the pulse shaper. The x-axis is labeled by the resonance excited by the applied spectral phase. This resonance is changed by adding a linear phase to the red half of the spectrum. There is a transfer of photons from the blue half of the laser spectrum to the red. The opposite effect appears to occur at higher frequencies, but is in fact indicative of the same process occurring in the reference pulse, whose phase is the sum of the selective excitation and that due to extra dispersion, shown in FIG. 5. The location of this reversal can be tuned by changing the amount of dispersion in the reference arm of the interferometer. The resolution is determined by the pulse shape. The signal to noise might be improved slightly by tailoring the spectral range of the laser for each excitation frequency.

Figure 4:
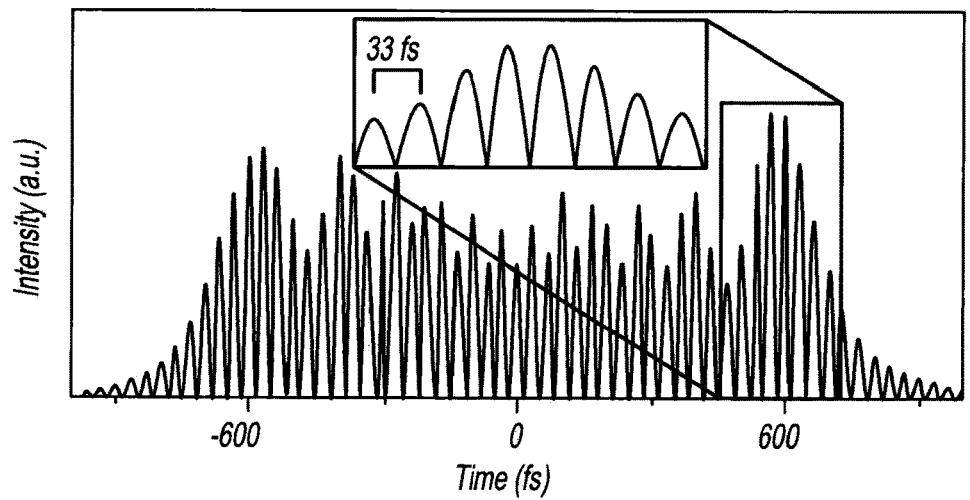
FIG. 4 is a graph showing an expected time domain intensity profile using the present laser system.
Figure 5:
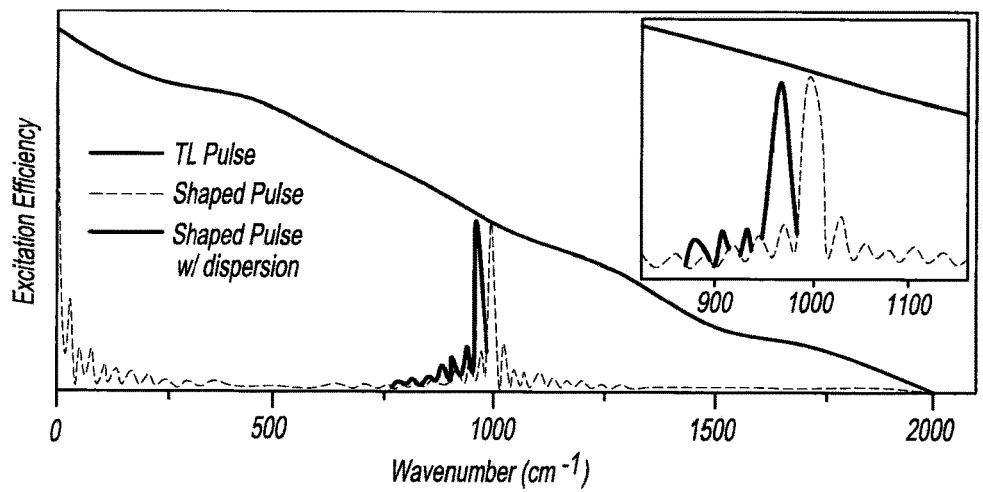
FIG. 5 is a graph showing a calculated excitation efficiency of the main and reference pulses using the present laser system.

To achieve maximum excitation efficiency and improve signal to noise, the laser spectrum should cover a range of twice the frequency of interest, for example, cut to 2000 cm⁻¹ to excite 1000 cm⁻¹ as in FIG. 4. A narrower spectrum will reduce the signal. Too broad of a spectrum will deliver unnecessary laser light from the wings of the spectrum. Nevertheless, this could be circumvented by adding more cycles to the periodic phase mask, producing greater numbers of vibrationally excited molecules, but detection of this additional excitation can be hindered by competition between SRL and SRG in the central region of the laser spectrum.

Figure 7:
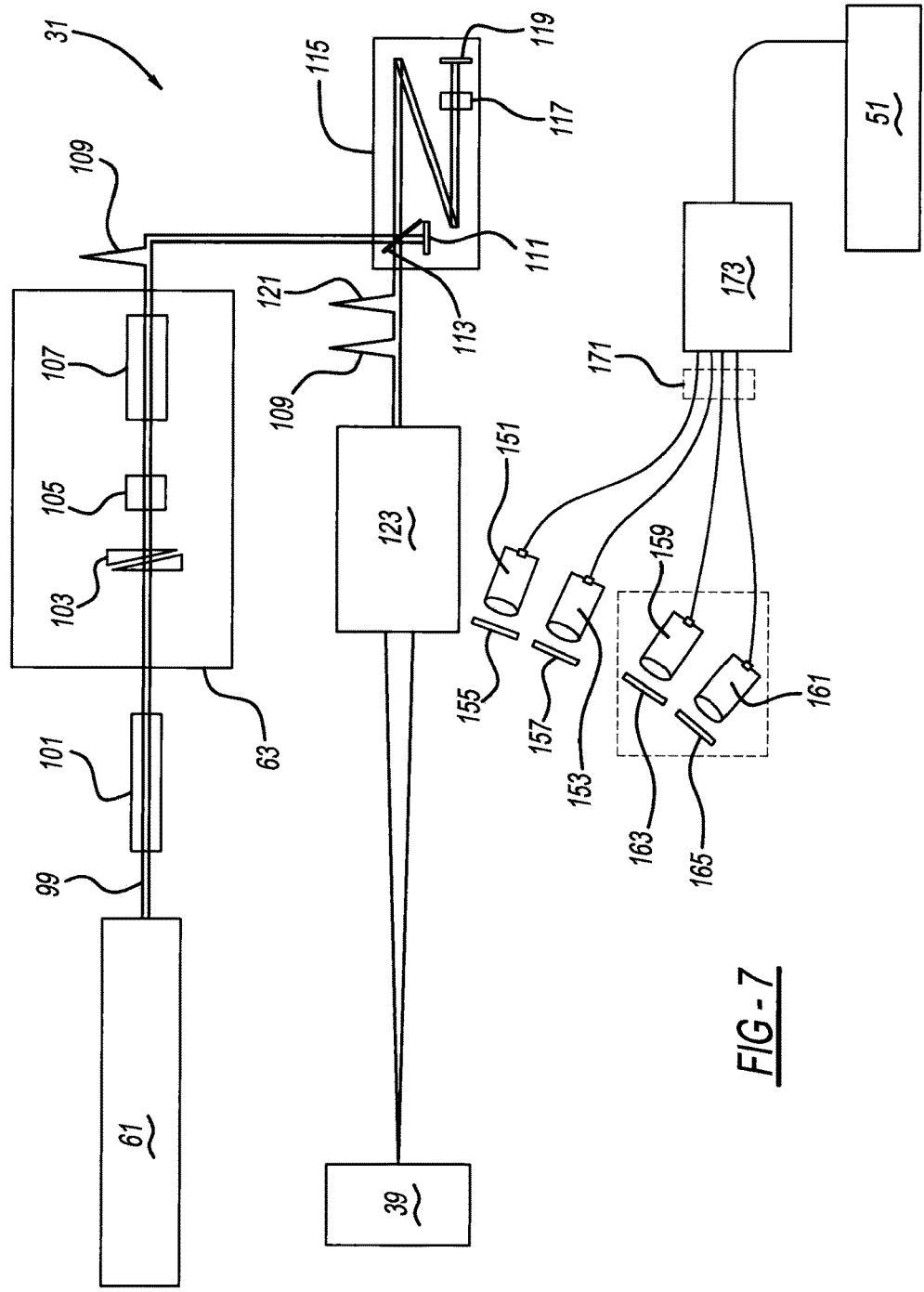
FIGS. 7-10 are diagrammatic views showing various commercial embodiments of the present laser system.

FIGS. 7-10 depict various configurations of a commercial setup for the present laser system 31 for use on a clothing/luggage/parcel specimen 39 at security scanning station such as that in FIG. 1. In the embodiment of FIG. 7, laser 61 emits greater than 10 nJ, 500 fs or less duration main laser pulse with a 1 MHz repetition rate. More preferably the pulse energy is 10-10,000 nJ and even more preferably 30-10,000 nJ, depending on the repetition rate; the greater the repetition rate, the lower the energy per pulse. Alternately, the pulses can have an average intensity of 0.01-1 Watt.

A highly-nonlinear fiber 101 acts as a bandwidth broadening optic for the main laser pulse 99. Optics 63 include a pair of opposed birefringent wedges 103, having fast access at 45°, a 0° polarizer 105 and a glass rod optic 107, serving as a dispersion introducing element. Wedges 103 are translated or moved to change the excited resonance and such wedge translation can be automatically computer controlled or manually actuated. This creates a tailored main or initial laser pulse 109 having the desired phase characteristics to cause Raman vibrations of a target molecule or particle, such as an explosive, on specimen 39 when received thereat. The main pulse 109 may also consist of a train of identical sub-pulses as is shown in FIG. 21. The main pulse 109 is then reflected by a mirror 111 and beam splitter 113 inside a replicator 115, here, a folded delay arm, which includes another dispersion introducing element or optic 117 and a reflective mirror 119. This causes a detuned reference pulse 121 (or train of sub-pulses as shown in FIG. 21) to be created in a temporally delayed manner, with essentially an identical energy and spectra to the main pulse, but with a different spectral phase so as to not excite or vibrate a Raman portion of the target molecule, as compared to main pulse 109. Scanning and auto-focus optics 123 are employed to transmit the main and secondary reference pulses 109 and 121, respectively, onto specimen 39.

A first set of photodetectors 151 and 153 are preferably photodiode sensors with a long wavelength (for example, red light) long pass filter 155 and a short wavelength (for example, blue light) short pass filter 157. Lens may also be employed for the photodetectors. These photodetectors have a high dynamic range and are fast enough to clearly distinguish between the primary and reference pulses reflected from specimen 39. Optionally, one or more additional sets of photodetectors 159 and 161, including a long pass filter 163 and short pass filter 165, may also be employed to provide redundant information, especially over a larger specimen while also serving to reduce false positive signals. Auto-focusing optics and lenses may also be provided on each photodiode to enhance signal collection. An optional amplifier 171 and a digitizer 173 connect each photodetector to computer controller 51 via an electrical circuit therebetween.

Figure 8:
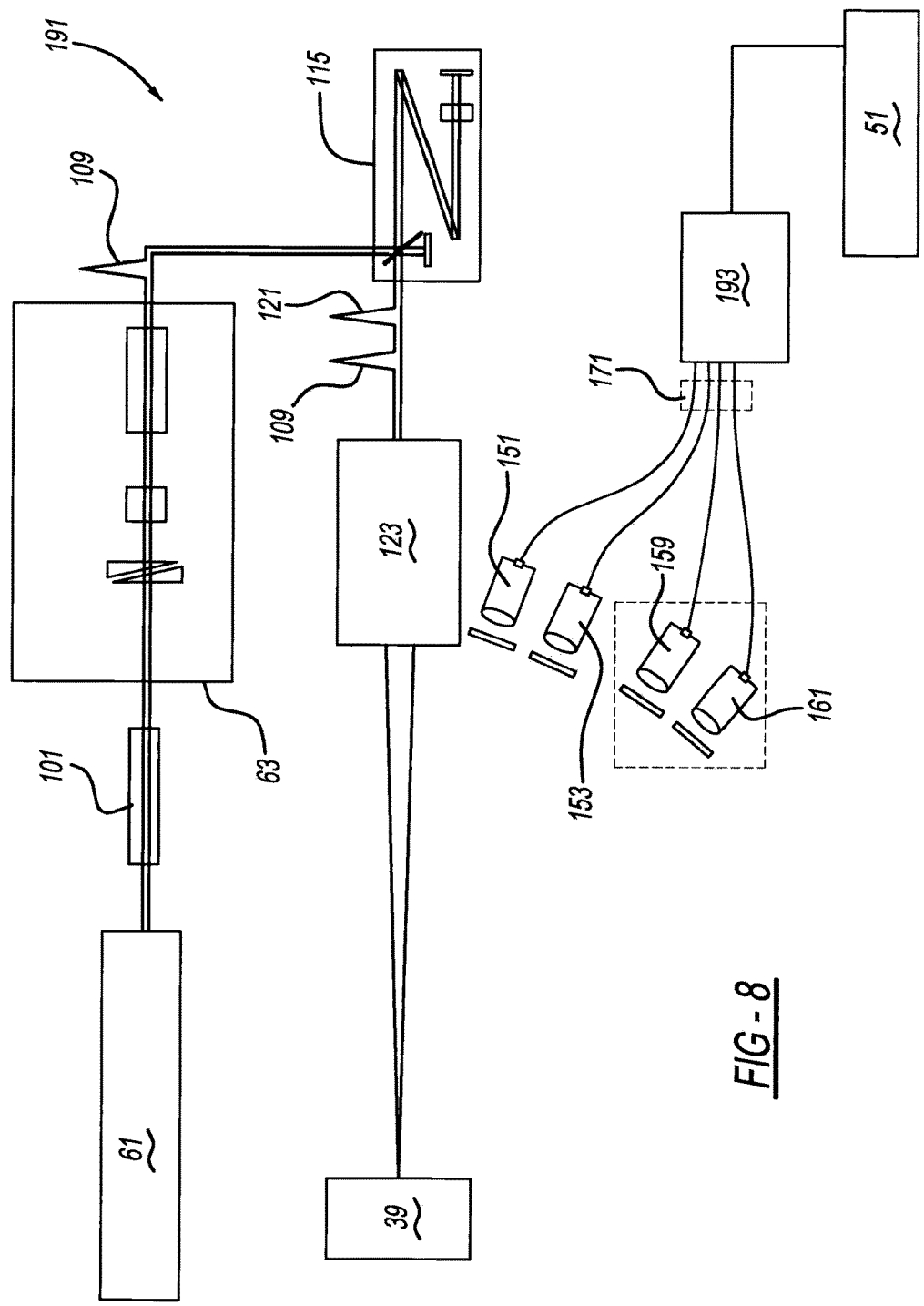

FIG. 8 shows another embodiment of laser system 191. This configuration is essentially the same as that of FIG. 7, however, an analog signal processor 193 is employed instead of the FIG. 7 digitizer. This analog system processor 193 is advantageous where high-speed signals are required between the detectors and computer 51. No pulse shaper is needed given the optics 63 which includes the birefringent wedges.

Figure 9:
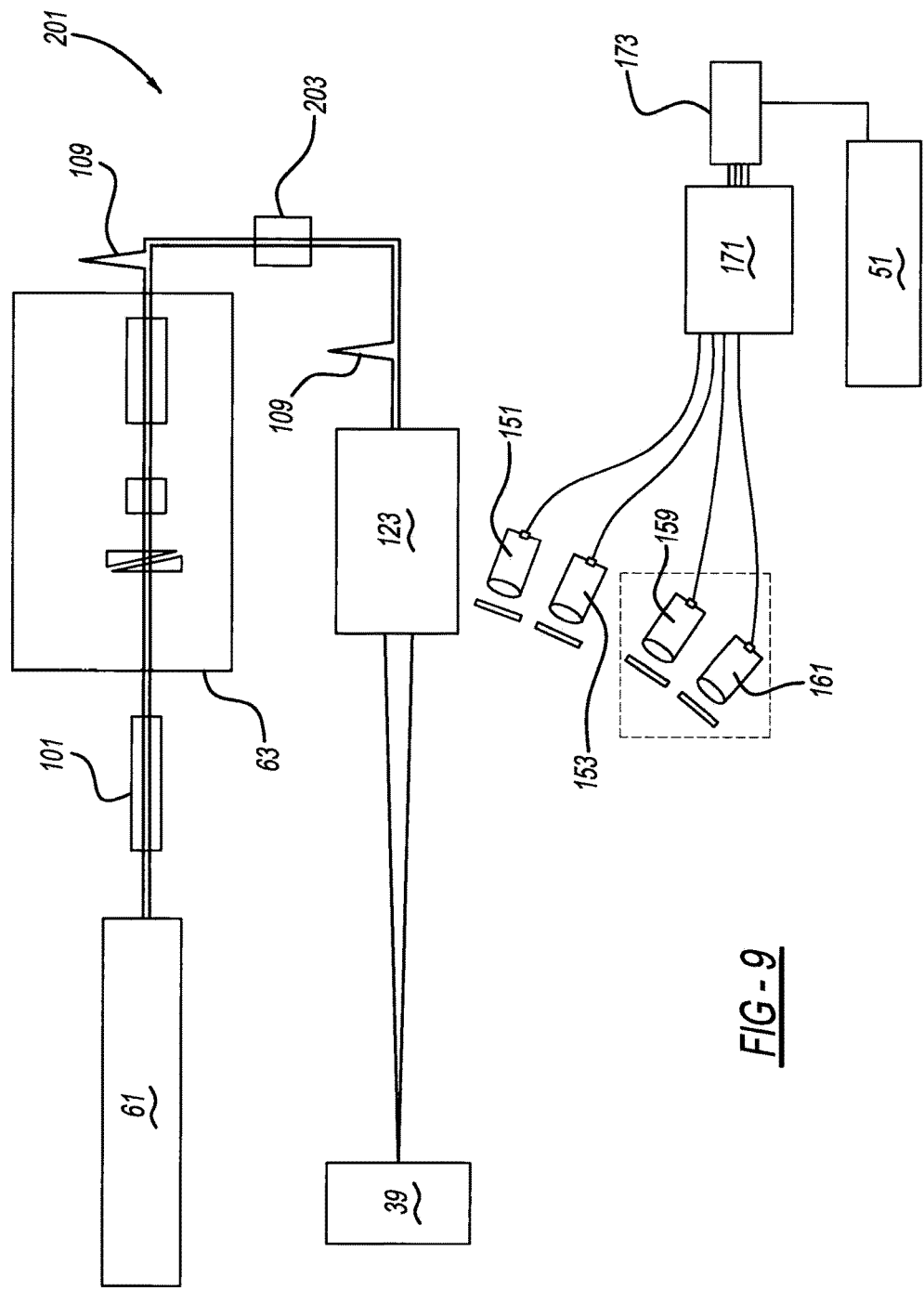

FIG. 9 illustrates another commercial setup alternative that is similar to that of FIG. 7. Notwithstanding, this laser system 201 employs a high-speed dispersion control unit 203, such as an acousto-optic device, instead of a pulse replicator 115 (see FIG. 7). This dispersion control unit 203 alternates between two values at a high rate, and of the same frequency as for a narrow frequency band amplifier 171.

Reference should also be made to FIG. 22, where it is shown that this approach employs high-speed modulation instead of a delayed replica. A phase is modulated instead of the amplitude of wavelength. In other words, in this version, a high repetition rate laser is used, and instead of creating a delayed reference pulse, the next pulse coming from the laser is used for the reference: every other pulse is a reference. The modulator operates at the repetition rate of the laser, and may be a Pockell cell that is driven between two polarizations and functions as a gate to cause further dispersion on the pulse. The pulses cannot be exactly the same or no difference will be measured, so the reference pulse uses the same "added dispersion" trick to detune the excitation. Thus, dispersion is added to every other pulse using a fast dispersion modulating device. By amplifying the signal at a frequency of half the repetition rate of the laser, the controller is effectively calculating the average value of (pulse minus reference pulse). Note that the same thing can be accomplished passively by inserting the (folded delay arm+dispersion producing element) instead of the (high speed dispersion control). Then the amplifier should be set at the frequency equal to the rep-rate of the laser. Furthermore, if the (high speed dispersion control) is used, the modulation does not have to occur at half the laser repetition rate; it can be modulated at arbitrary frequency (preferably high) and the signal amplified at this arbitrary frequency. Frequency domain detection (amplifying the signal at a particular frequency as above) will eliminate some of the detection flow chart options, as statistics will not be calculated. Accordingly, the software logic and methods of FIG. 11 (as will be described in greater detail hereinafter) works best with this configuration since there are no statistics gathered in lock-in style detection.

Figure 10:
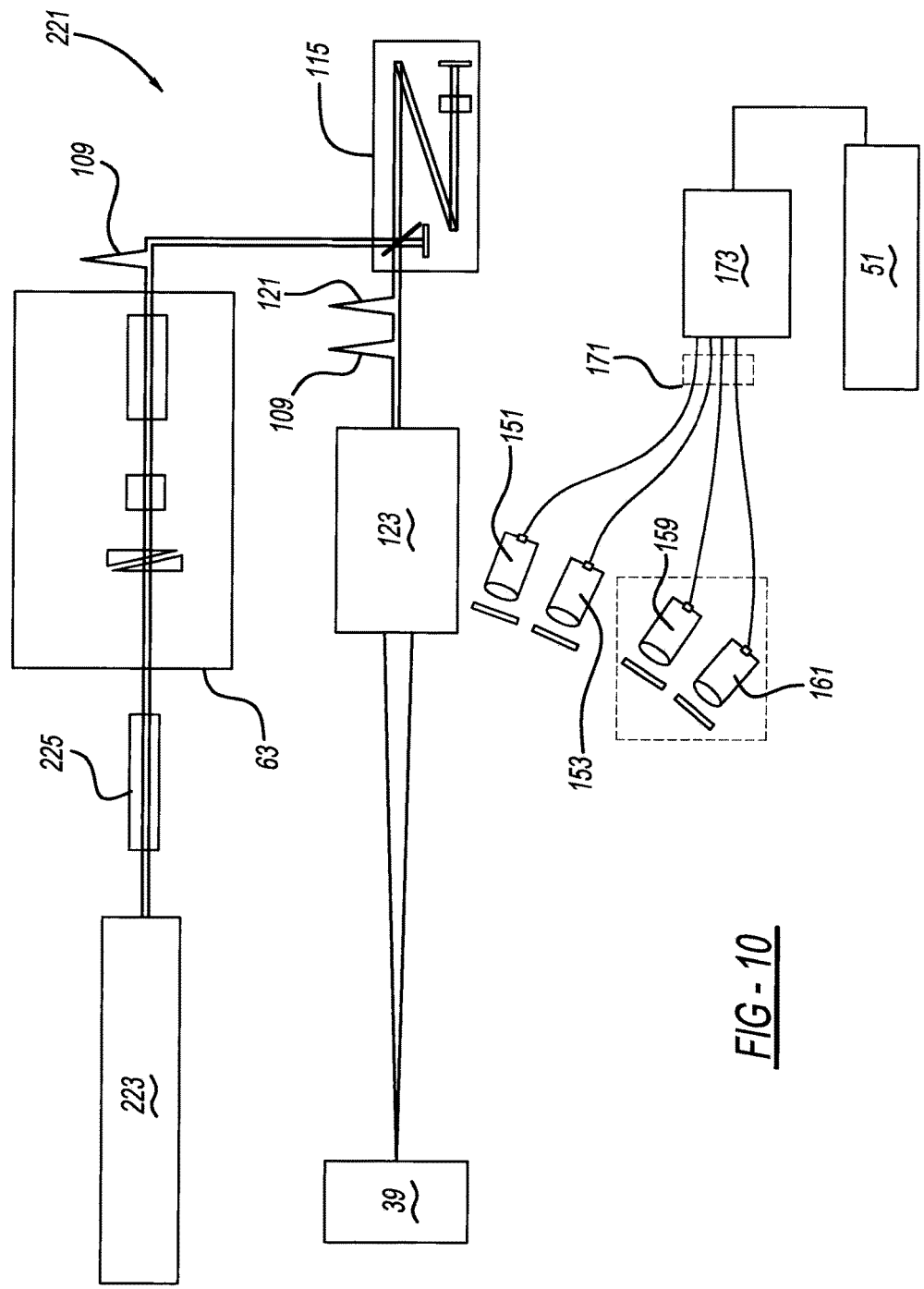

Next, another commercial setup of the present laser system 221 can be viewed in FIG. 10. This laser system 221 is very similar to that of FIG. 7, however, a 1 mJ, 10 kHz repetition rate laser 223 emits ultrafast laser pulses of 40 fs or greater. Furthermore, a hollow waveguide 225, with Nobel gas therein, serves as the bandwidth broadening optic. No pulse shaper is needed with this embodiment.

A preferred laser source for single-beam-SRS is disclosed in K. Wang, et al., "Advanced Fiber Soliton Sources for Nonlinear Deep Tissue Imaging in Biophotonics," IEEE Journal of Selected Topics in Quantum Electronics, vol. 20, no. 2 (March/April 2014). This laser system consists of an industrial 1.5 μm chirp-pulse amplification fiber laser producing sub-500 fs pulses (obtained from Calmar under model no. FLCPA-01C). Alternately, a high-power (e.g., 1000 nJ or greater per pulse) oscillator can replace the Calmar amplified laser above wherein this replacement oscillator is much more compact, rugged and simple compared to the amplified source. The Wang laser produces broadband pulses that are thereafter converted in the present system into multiple pulses by changing its phase so that it produces a train of pulses that essentially match a phonon frequency. The present system also creates a reference pulse, which is broken into another train of pulses that do not match the Raman vibrational frequency. The output of the Wang laser is coupled to a large mode area fiber (an example of which can be obtained from Thorlabs as model no. LMA35) or an ultra large mode area photonic crystal fiber rod (for example DC-285/100-PM-Yb-ROD from NKT Photonics) where soliton self-frequency shifting ("SSFS") takes place to create a coherent supercontinuum. 60 nJ can be obtained when filtering wavelengths above 1.6 mm. Such energies should be sufficient for standoff distances <3 m in the present use. Much longer distances are possible when the energy is raised to at least 300 nJ. It is envisioned that the resulting Single Ultrafast Excited Remote ("SUPER")-SRS system is rugged, compact, eye-safe, and faster than prior laser-based Explosives Trace Detection ("ETD") systems.

The computer software instructions and logic methodology, usable with most of the prior setups, are disclosed in FIGS. 11-20. These computer software instructions are stored in the non-transient memory of computer controller 51. The logic diagram and method steps of FIG. 11 control the pulse shaper by applying an appropriate spectral phase to the pulse. It also uses the selected and detected reflected light from the photodiodes to make the appropriate signal calculations in order to factor out the background chemical environment noise, minimize the reflected light scatter from the fabric or paper specimens so that a stronger detected/collected signal can be used, and it helps to distinguish the detected/collected signal between a targeted explosive Raman vibration in another chemical that is not Raman vibrated. In other words, the software causes the computer controller to compare the on-resonance scatter difference (blue/red) versus the off-resonance signal. The on-resonance signal comes from the main first pulse as it resonantly excites one or a few vibrations. The off-resonance signal comes from the delayed replica pulse. The computer controller and software therein distinguish them since the delay is in nanoseconds and they receive and resolve the photodiodes' signals in time. Furthermore, the amount of scatter or absorption of the diffused light by the specimen changes the overall intensity of the scattered light detected. The software and controller need the reference signal to normalize such so that the system only determines the existence of an explosive particle without being confused by changes in scattering properties of the target specimen. Because both pulses are co-linear and focus on the same spot, the software and controller are able to normalize changes in scattering properties of the sample. It is noteworthy that the normalization of the detected signal is based on making the signal independent of scatter intensity, but not necessarily to reduce scatter.

Finally, in order to assist with the identification calculation of the targeted (e.g., explosive) molecule or particle, the software and controller normalize the total scatter and make it more sensitive to energy transfer from high frequency to low frequency photons, in other words blue to red wavelengths. If the explosive particle is detected then the computer controller will automatically flash warning light 55 (see FIG. 1), activate an audible alarm or the like. If such a targeted particle is not detected, then the computer controller will automatically cause the laser to emit a new pulse for subsequent detection and scanning.

Figure 11:
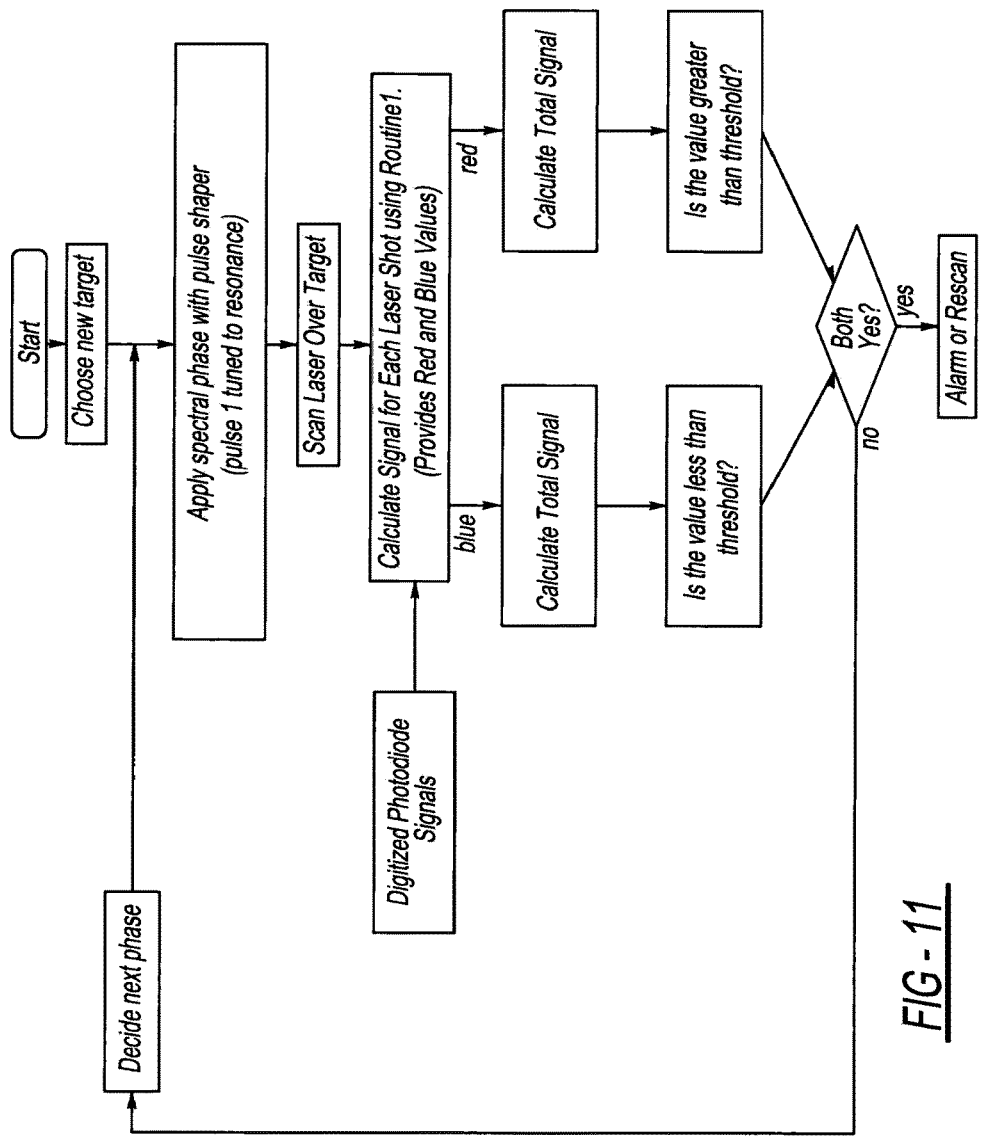
FIGS. 11-20 are logic flow diagrams for programmable software instructions used in the present laser system.
Figure 12:
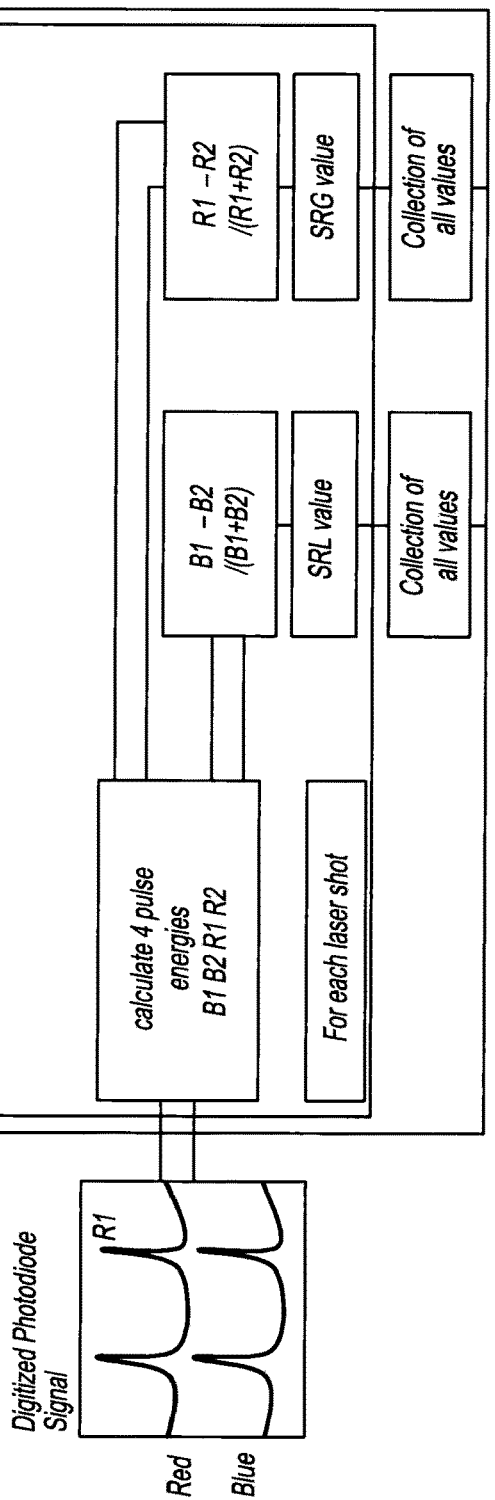

FIG. 12 illustrates the software flow logic for the Routine 1 employed in the software instructions of FIG. 11. This demonstrates the logic for calculating the four or more pulse energies received by the photodiodes. B1 and B2 indicate two different blue wavelength signals and R1 and R2 designate two different red wavelength signals from the collected spectra reflected by the specimen. Energy transfer through SRG or SRL are calculated according to the ratio between the signals $SRL=(B1-B2)/(B1+B2)$ and $SRG=(R1-R2)/(R1+R2)$.

Figure 13:
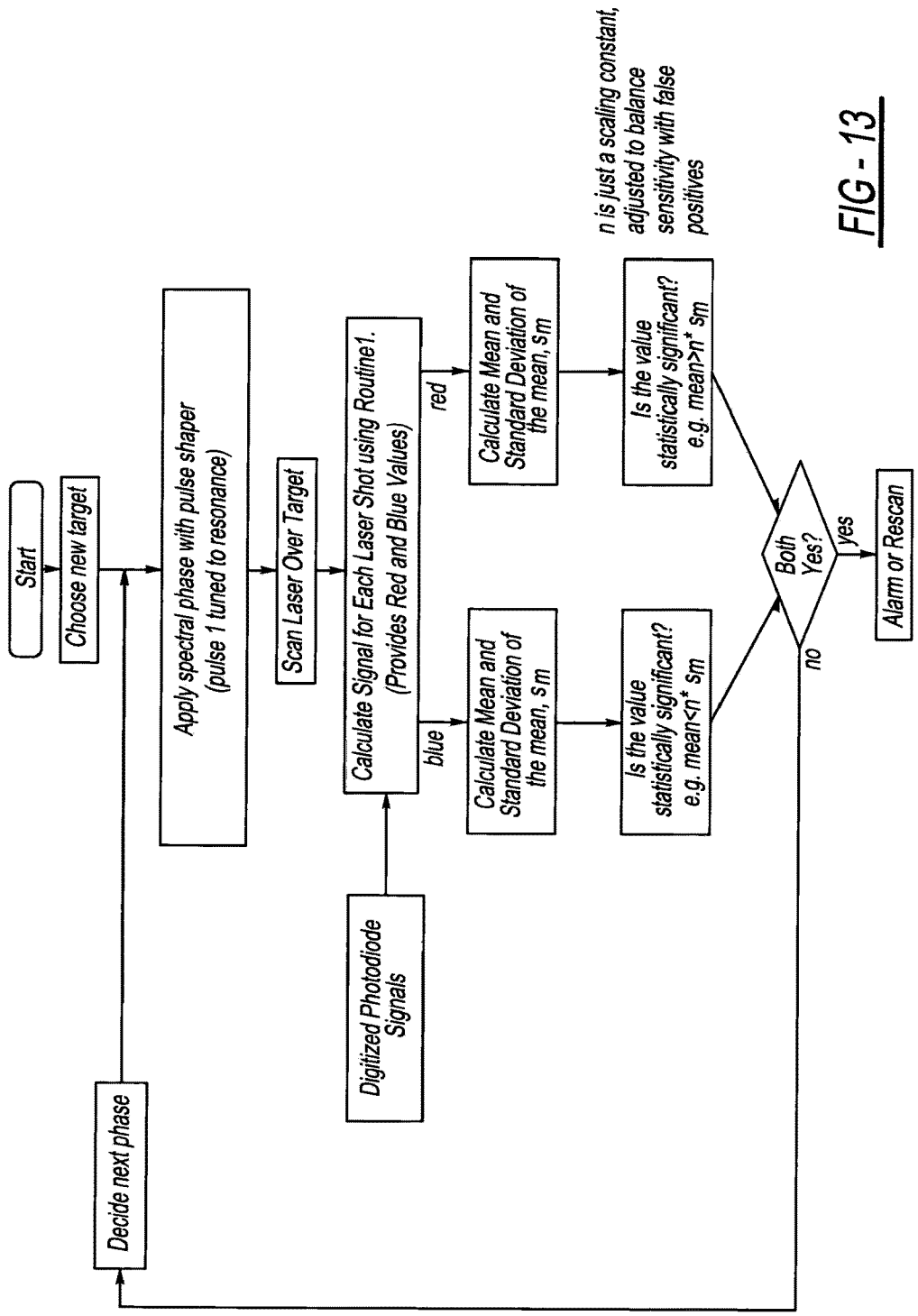
Figure 14:
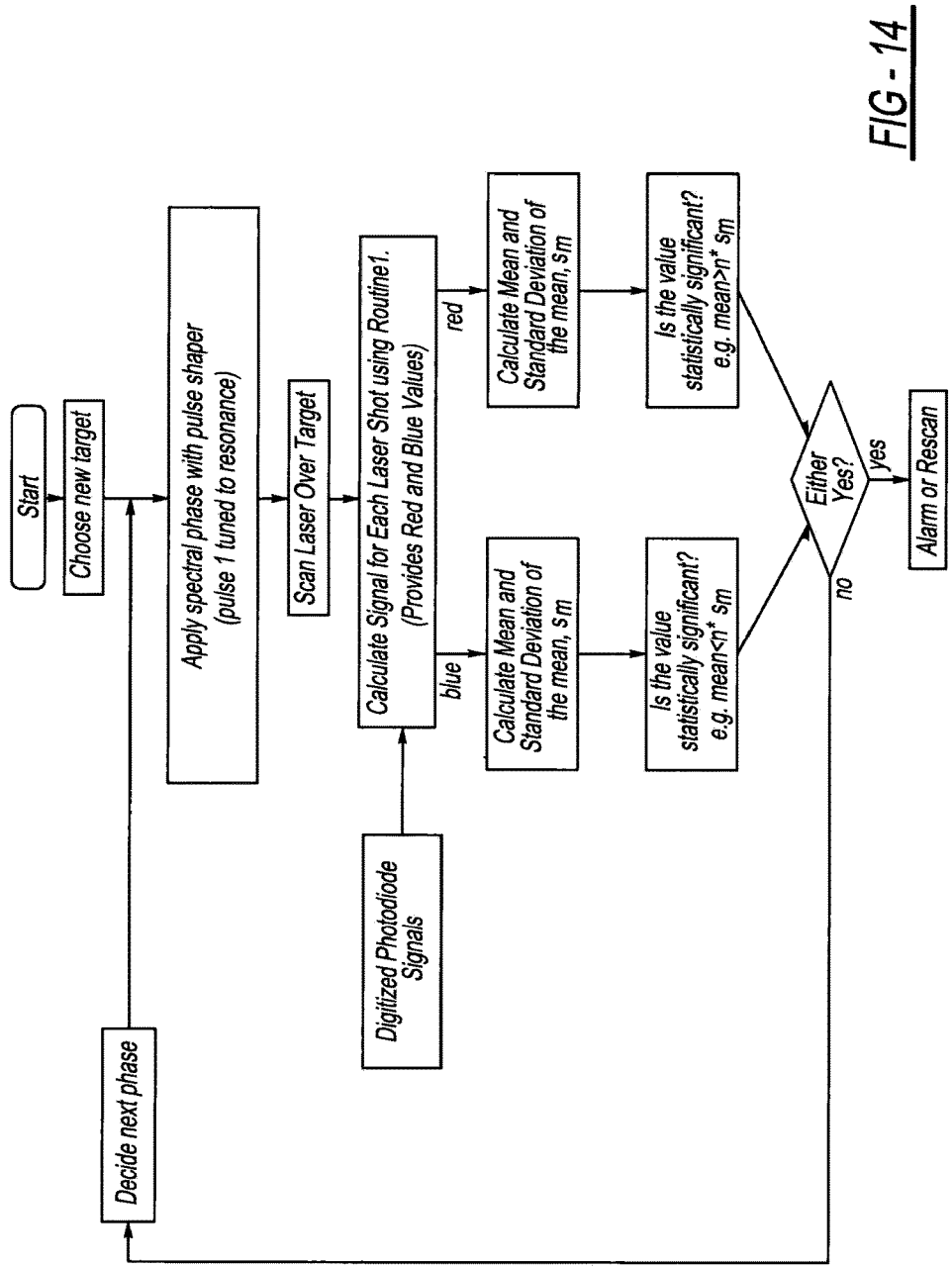

FIG. 13 illustrates another version of the computer software instructions and logic. This methodology is similar to that of the prior embodiment; however, additional statistical processing is employed in order to balance sensitivity with false positive reduction. FIG. 14 is essentially the same as that for FIG. 13, but near the illustrated bottom, the software and controller consider either side of the spectra while the methodology of FIG. 13 considers both sides of the spectra.

Figure 15:
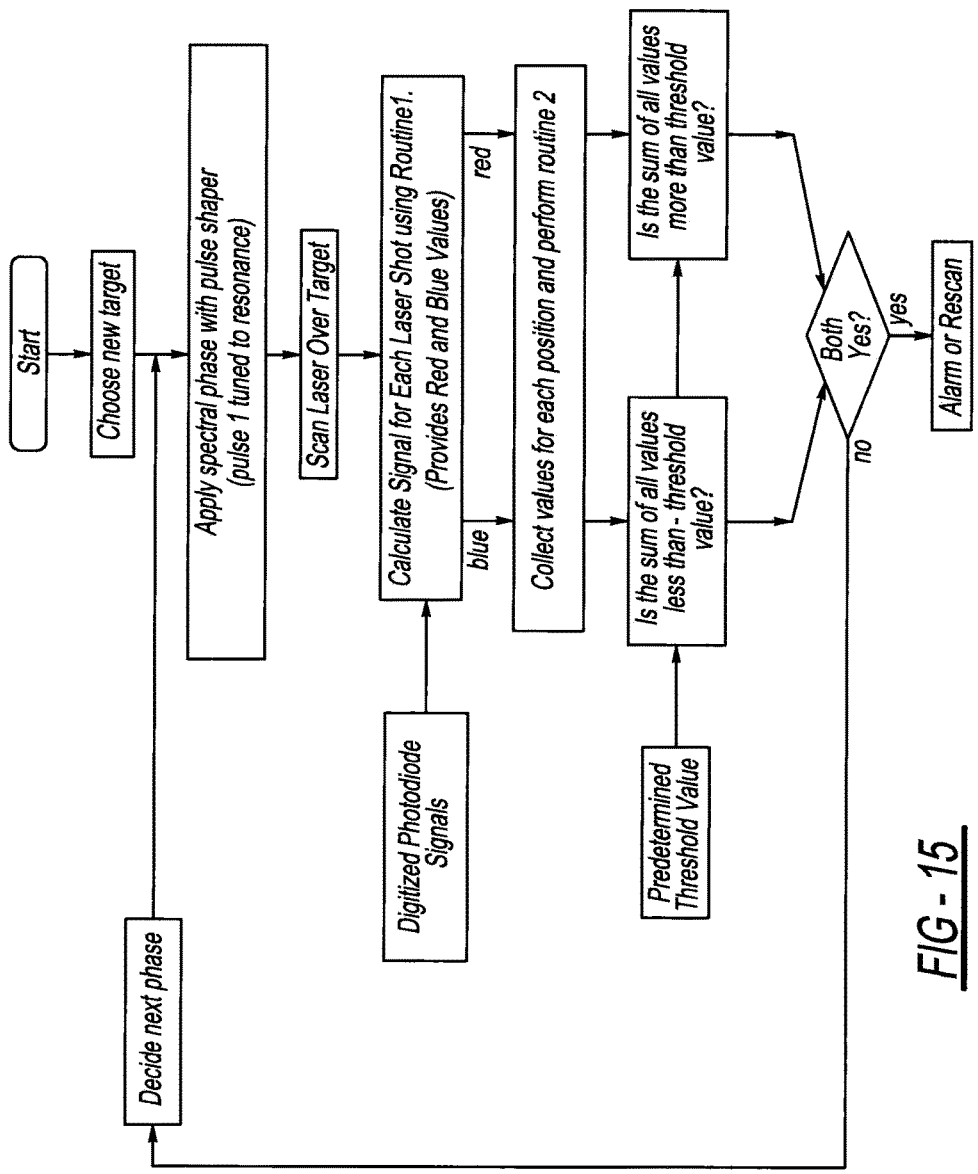
Figure 16:
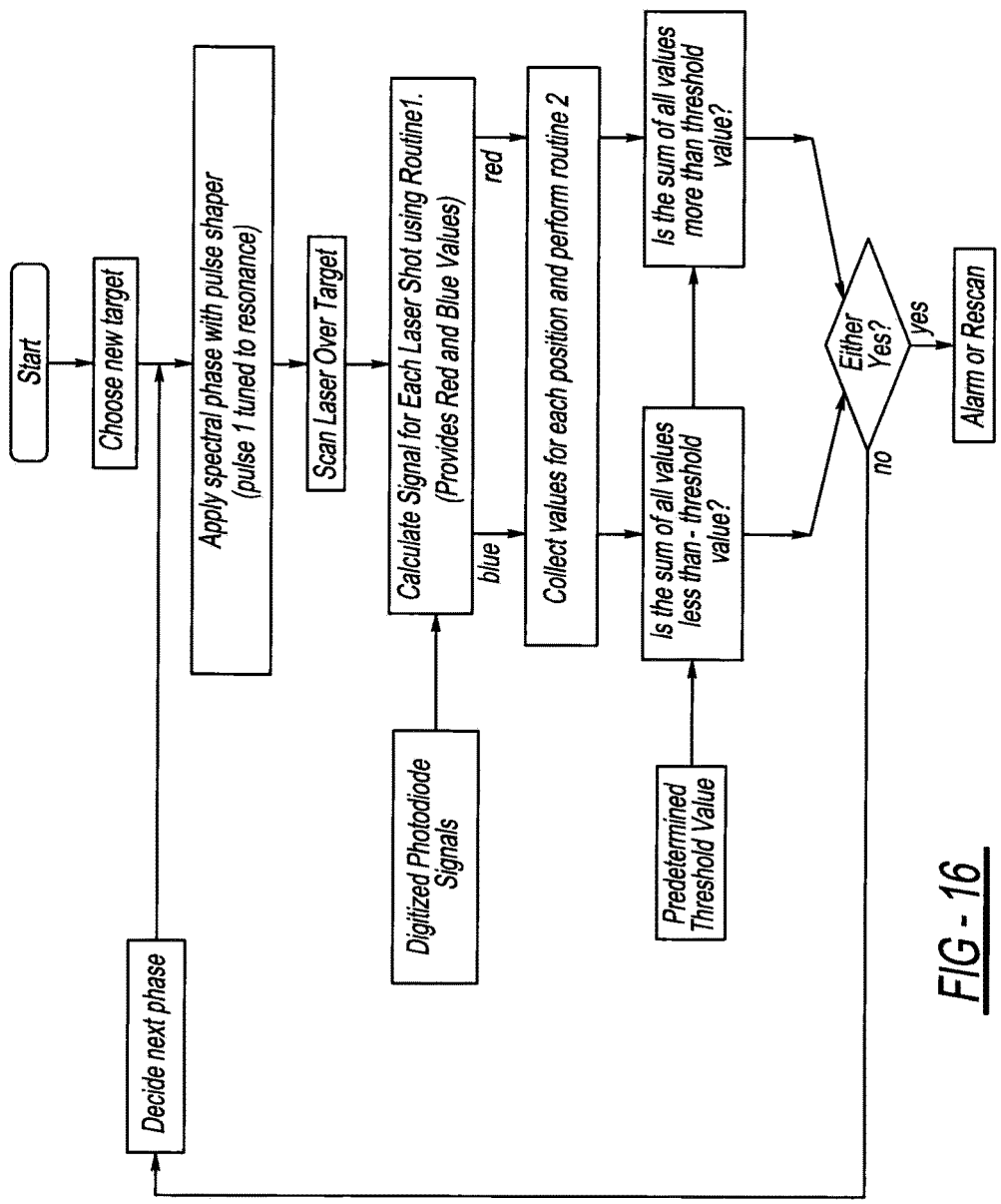
Figure 17:
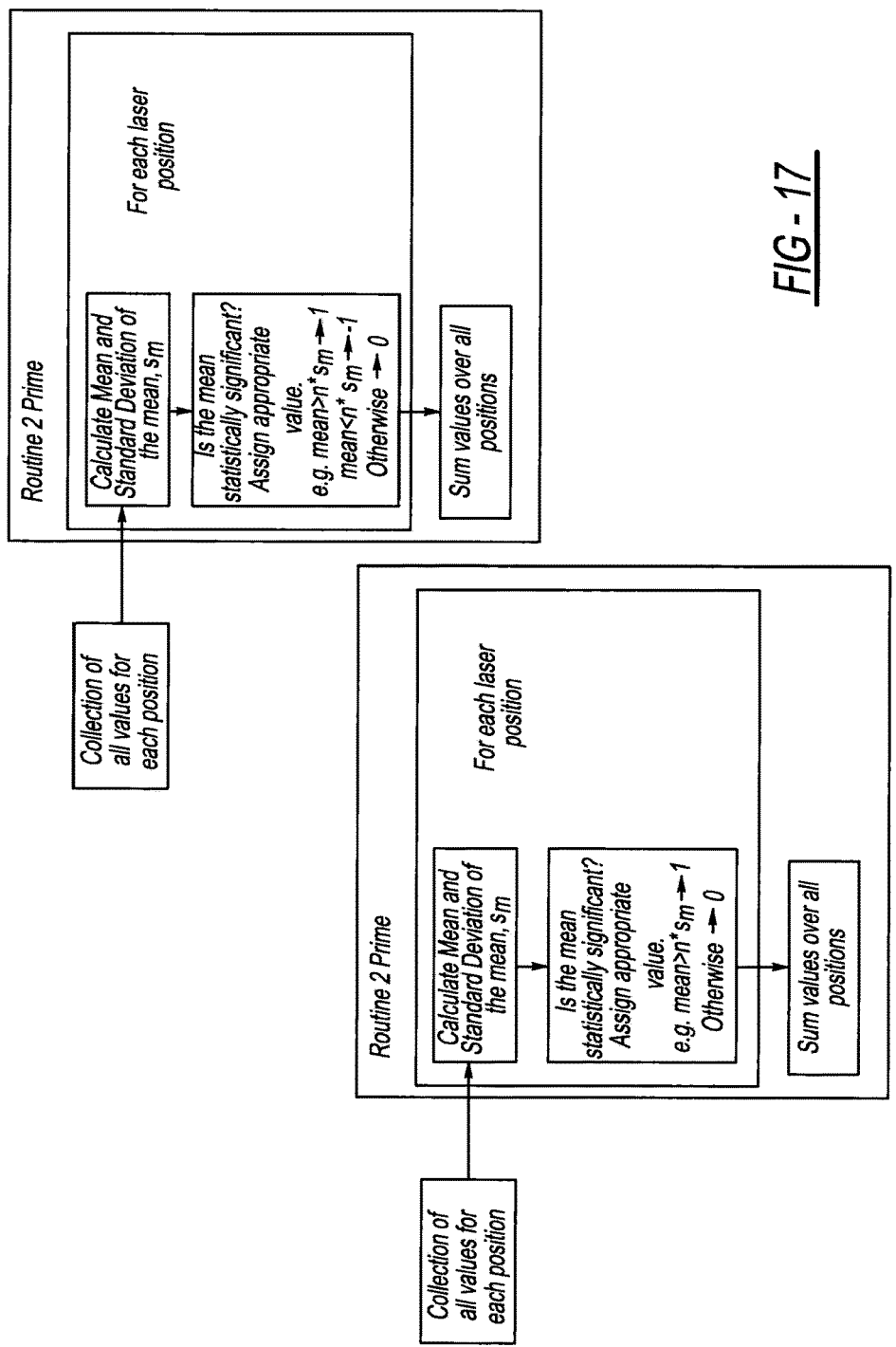

FIGS. 15 and 16 illustrate more sophisticated versions of the computer software instructions and methods. They employ the Routines 1 and 2 of FIGS. 12 and 17. These versions are more discriminating on their sensitivity and for minimizing false positives. It is worth noting that FIG. 15 considers both sides of the spectra while FIG. 16 considers either side of the spectra.

Figure 18:
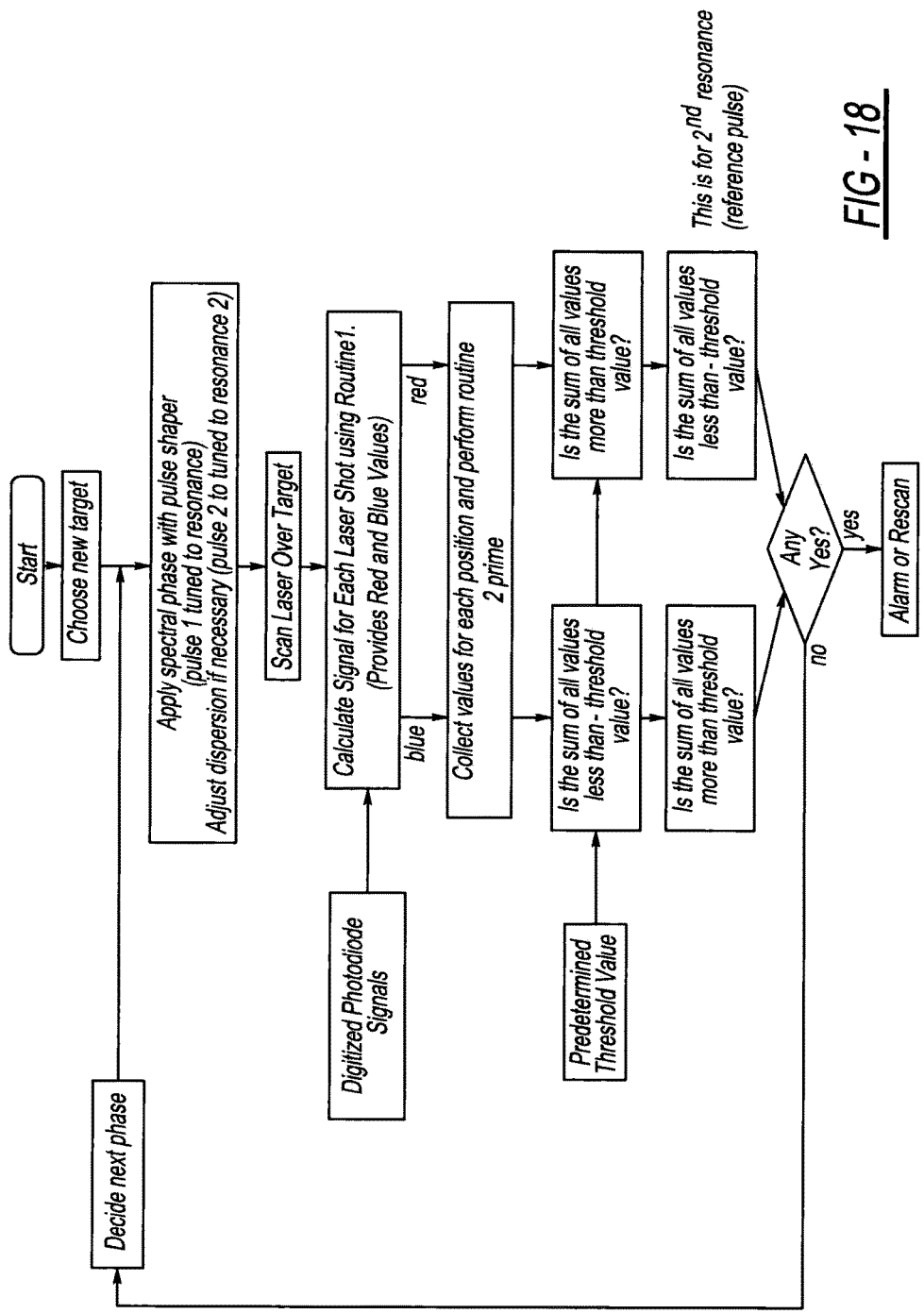
Figure 19:
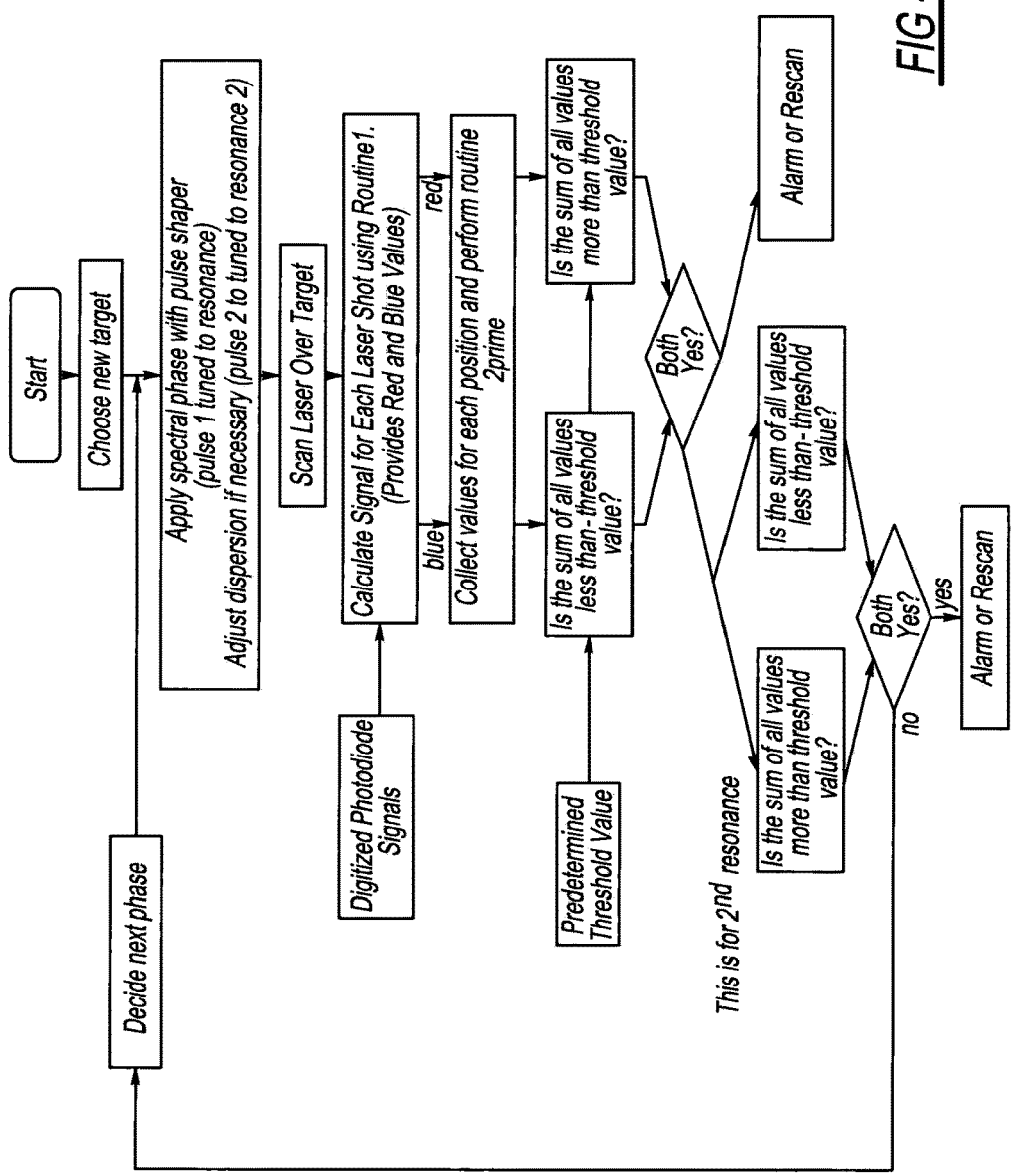

FIGS. 18 and 19 are even more sophisticated computer software instructions and methods employed with the present laser system. These are used with multi-component approaches where the reference pulse is detuned by the dispersion. An appropriate amount of dispersion will tune the second replica pulse to another resonance of interest, such as a second type of explosive compound or harmful biological agent, by way of example. Thus, two or more resonances are scanned at the same time in order to obtain faster operation and identification of harmful particles on the specimen. Notwithstanding, these methods assume that there will not be two harmful compounds of interest on the same specimen. FIG. 18 considers either wavelength half of the spectra while FIG. 18 considers the entire spectra.

Figure 20:
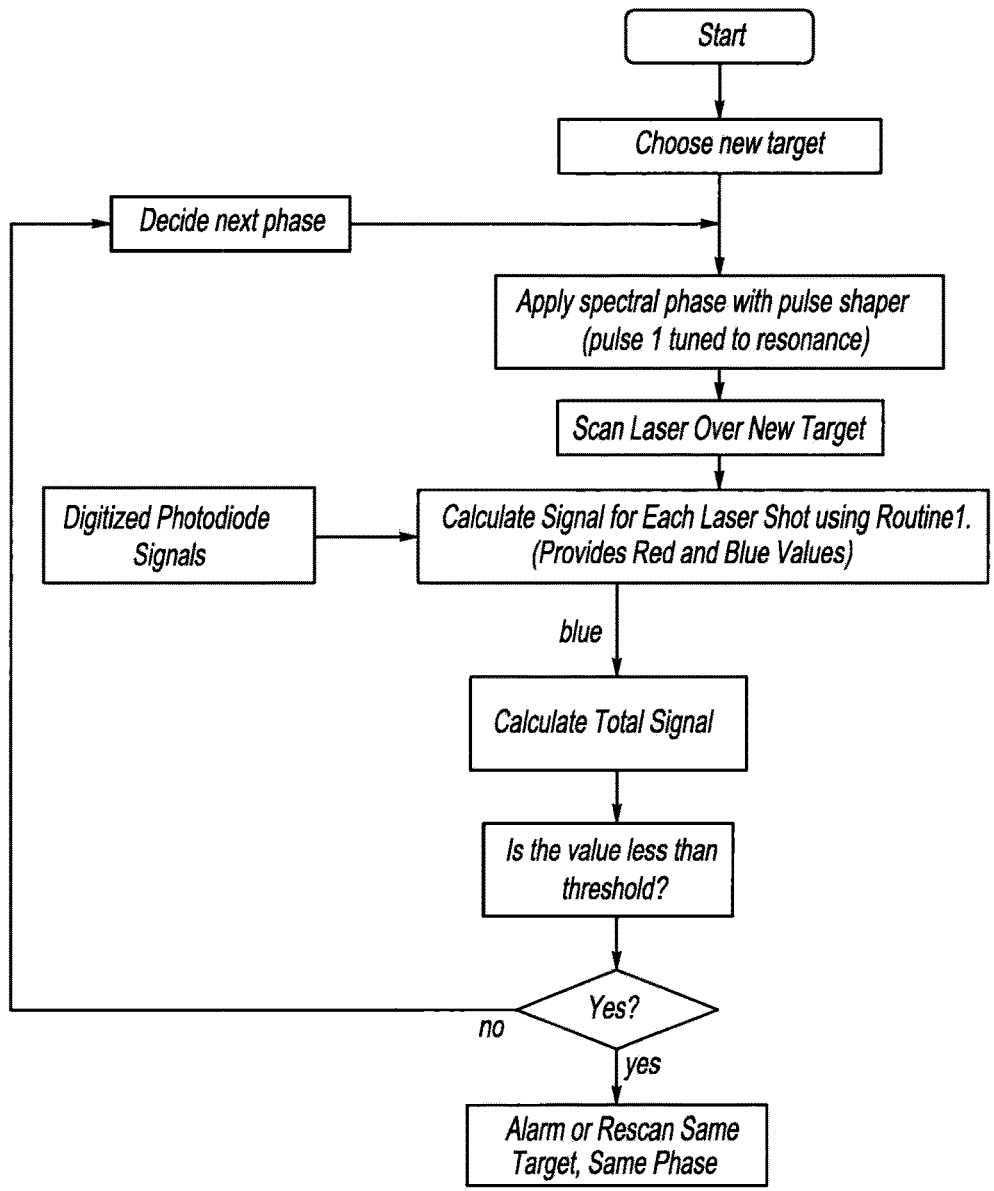

The software instructions and methods shown in FIG. 20 are for a simplified filtering system. This is more appropriate for use with the setup of FIG. 9, but with a filter for blocking the red portion of the pulse employed instead of the dispersion element 203 (see FIG. 9). Alternately, the blue wavelength could be blocked and the red signals analyzed.

While various embodiments have been disclosed hereinabove, it should be appreciated that additional variations may be made. For example, other types of active or passive pulse shapers may be employed although certain advantages may not be obtained. The system can be used to monitor a single type of explosive or it can be programmed to search for an entire list of hazardous and non-hazardous materials according to their vibrational frequencies. Alternatively, the system may be used to detect hazardous nanoparticles on surfaces such as clothing or human skin. Accordingly, the present system has the ability to selectively excite two or more Raman vibrations simultaneously or one-at-a-time in a serial manner. Additionally, the present laser system may be used in microscopy (for imaging tissues with cellular resolution) or without a standoff distance to the specimen, however, many of the present security screening advantages will not be realized. When used for microscopy, the laser system will achieve higher sensitivity than prior SRS implementations, and the new use of a detuned reference pulse will ensure that contrast will primarily arise from molecular composition and not from scattering or density changes in the biological tissue. Furthermore, the laser system can be moved over a stationary specimen, such as at a cargo port or the like. While pairs of photodiodes are disclosed, a more basic construction employs a single photodiode, although some advantages may not be obtained. Furthermore, it is envisioned that the pulses can be shaped without a dedicated pulse shaper, although some benefits may not be achieved. Alternately, the source of laser pulses may be an open air, fiber, or diode laser, depending on the desired pulse energy, duration and wavelength. While shorter wavelengths are conducive to greater Raman scattering signals, wavelengths that are shorter than 300 nm or longer than 1.4 micro-meters are considered eye safe, and therefore advantageous. It should be further appreciated that any of the structural, functional or software features of any of the embodiments may be interchanged with any of the other embodiments disclosed herein unless explicitly excluded, but certain advantages of doing such may not be obtained. Equivalent changes, modifications, variations in specific embodiments, apparatus, systems, compositions, materials and methods may be made within the scope of the present invention with substantially similar results. Accordingly, the examples and embodiments described herein are exemplary and are not intended to be limiting in describing the full scope of apparatus, systems, compositions, materials, and methods of this invention. Such changes, modifications or variations are not to be regarded as a departure from the spirit and scope of the invention.

The invention claimed is:

1. A method of using a laser system, the method comprising:
    (a) emitting a main laser pulse;
    (b) shaping the laser pulse which is subsequently used to selectively excite a desired Raman vibration through stimulated Raman scattering, when the associated target is present;
    (c) creating a delayed replica reference pulse from the main pulse, the main and reference pulses being substantially identical in energy and spectrum;
    (d) focusing the main and reference pulses;
    (e) collecting diffuse laser scatter such that relative intensities of at least one spectral half of the scatter generated by each of the main and reference pulses are received and identified by at least one photodetector;
    (f) calculating stimulated Raman loss and/or stimulated Raman gain from the collected reflected laser scatter;
    (g) using the calculated value associated with the reference pulse to reduce undesired contributions from the calculated value associated with specimen absorptivity and texture; and
    (h) automatically determining if a substance trace is present, after at least step (e).

2. The method of claim 1, further comprising:
    (a) moving at least one of: a fabric specimen and a security screening structure, relative to the other;
    (b) diffusely scattering the main and reference pulses, emitted from at least one laser coupled to the structure, from the fabric specimen; and
    (c) using at least two of the photodetectors coupled to the structure to collect the laser scatter, the photodetectors detecting different spectrum wavelengths of the laser scatter.

3. The method of claim 2, further comprising using the calculations and determination of a programmable controller to initiate an alarm if the substance, which is an explosive, is present on the fabric specimen, within three seconds from the emitting of the main laser pulse, and without coherent anti-Stokes Raman scattering and without Raman spectroscopy.

4. The method of claim 2, further comprising:
    (a) receiving a lower energy portion of the spectrum of the main and reference pulses with a first of the photodetectors, which is a photodiode;
    (b) receiving a higher energy portion of the spectrum of the main and reference pulses with a second of the photodetectors, which is another photodiode; and
    (c) using a programmable controller to determine a Raman active phonon transfer of energy manifested as an increase in the laser scatter in a lower energy portion of the spectrum and a decrease in a higher energy portion of the spectrum.

5. The method of claim 1, wherein:
    the focusing causes a laser spot size of 5-1,000 microns, inclusive, at a specimen;
    the emitted main and reference pulses each have a pulse energy of at least 30 nJ; and
    the specimen is located at least 0.5 meters away from a laser doing the emitting and a photodetector doing the collecting.

6. The method of claim 1, further comprising amplitude shaping the reference pulse different from the main pulse.

7. The method of claim 1, further comprising eliminating at least some interfering non-linear signals, including two-photon absorption, through measuring essentially the entire spectrum scattered.

8. The method of claim 1, wherein the determining step further includes detecting the substance which is less than 100 µg of a hazardous substance, over at least 1 cm$^2$ area on a fabric surface, in a public transportation facility.

9. The method of claim 1, wherein the determining step further includes detecting a single explosive particle of the substance having a weight of about 15 ng or less, within 20 ms on fabric, using 1 W or less of laser power in the near infrared.

10. The method of claim 1, further comprising transmitting the main pulse through at least one of: a fiber and a waveguide, the shaping of the main pulse is done with birefringent wedges and a polarizer, the replicating of the main pulse to create the delayed reference pulse is done with a folded delay arm including a dispersion-introducing optic and a mirror, and the collecting uses a long-pass filter with a first photodetector and a short-pass filter with at least a second photodetector.

11. The method of claim 1, further comprising automatically moving a mirror relative to a screening checkpoint structure and a scanned specimen between laser pulse emission iterations, in order to vary directions of subsequent emitted pulses.

12. The method of claim 1, further comprising simultaneously exciting more than one target Raman vibration per emitted main laser pulse, if the associated targets are present.

13. The method of claim 1, further comprising serially exciting more than one target Raman vibration by a programmable controller automatically changing a subsequently emitted main laser pulse with a pulse shaper, if the associated targets are present.

14. The method of claim 1, further comprising transmitting the main and reference pulses through a microscope objective to image a tissue specimen with cellular resolution.

15. The method of claim 1, further comprising using a microprocessor to automatically determine stimulated Raman loss and stimulated Raman gain at least in part by calculating a ratio between the main and the reference pulses.

16. Software stored in non-transient computer memory, the software comprising:
    a first set of instructions adapted to cause a laser pulse to be emitted from a laser, shaped by a pulse shaper and then replicated in a time delayed manner by a pulse replicator such that a primary and a secondary laser pulse, having substantially identical energies and spectra, are targeted onto a specimen at least 0.5 m away;
    a second set of instructions adapted to receive signals associated with at least one spectral half of light diffusely scattered from the specimen, associated with each of the primary and secondary pulses, which are detected by at least one photodetector;
    a third set of instructions adapted to calculate at least one of stimulated Raman loss or stimulated Raman gain from the detected scattered light;

a fourth set of instructions adapted to minimize at least one of: distortions and background noise, in the detected reflected light by comparing values associated with the primary and secondary pulses, which have a different spectral phase; and a fifth set of instructions adapted to determine if a harmful substance trace is present on the specimen within three seconds of operation of the first set of instructions.

17. The software of claim 16, further comprising another set of instructions controlling and varying the pulse shaper, which is an active pulse shaper, to shape the laser pulse before the laser pulse is replicated.

18. The software of claim 16, wherein the specimen includes fabric or paper, the harmful substance is an explosive particle of about 15 ng or less, and 1 Watt or less of laser power is used.

19. The software of claim 16, further comprising another set of instructions moving a portion associated with the laser, which emits the laser pulse, at a transportation security checkpoint.

20. The software of claim 16, further comprising another set of instructions causing a visual alarm signal to be generated to an operator if the harmful substance is determined to be present at a transportation security checkpoint.

21. The software of claim 16, wherein the specimen is fabric.

22. The software of claim 16, wherein the specimen is paper.

23. A method of using a laser system, the method comprising:
 (a) moving at least one of: a specimen and a security screening structure, relative to the other;
 (b) emitting a main laser pulse;
 (c) shaping the laser pulse which is subsequently used to selectively excite a desired Raman vibration through stimulated Raman scattering, when the associated target is present;
 (d) creating a delayed replica reference pulse from the main pulse, the main and reference pulses being substantially identical in energy and spectrum;
 (e) focusing the main and reference pulses;
 (f) collecting diffuse laser scatter such that relative intensities of at least one spectral half of the scatter generated by each of the main and reference pulses are received by at least one detector;
 (g) calculating stimulated Raman loss and/or stimulated Raman gain from the collected reflected laser scatter;
 (h) using the calculated value associated with the reference pulse to reduce undesired contributions from the calculated value; and
 (i) automatically determining if a substance trace is present, after at least step (f), including detecting the substance which is less than 100 µg of a hazardous substance, over at least 1 $cm^2$ area on a fabric surface of the specimen, in a public transportation facility.

24. The method of claim 23, further comprising:
 (a) diffusely scattering the main and reference pulses, emitted from at least one laser coupled to the structure, from the fabric surface of the specimen; and
 (b) using at least two of the detectors which include photodetectors coupled to the structure to collect the laser scatter, the photodetectors detecting different spectrum wavelengths of the laser scatter.

25. The method of claim 23, further comprising using the calculations and determination of a programmable controller to initiate an alarm if the substance, which is an explosive, is present on the fabric surface of the specimen, within three seconds from the emitting of the main laser pulse, and without coherent anti-Stokes Raman scattering and without Raman spectroscopy.

26. The method of claim 23, wherein:
 the focusing causes a laser spot size of 5-1,000 microns, inclusive, at a specimen;
 the emitted main and reference pulses each have a pulse energy of at least 30 nJ; and
 the specimen is located at least 0.5 meters away from a laser doing the emitting and the detector doing the collecting.

27. The method of claim 23, further comprising amplitude shaping the reference pulse different from the main pulse.

28. The method of claim 23, further comprising eliminating at least some interfering non-linear signals, including two-photon absorption, through measuring essentially the entire spectrum scattered.

29. The method of claim 23, further comprising transmitting the main pulse through at least one of: a fiber and a waveguide, the shaping of the main pulse is done with birefringent wedges and a polarizer, the replicating of the main pulse to create the delayed reference pulse is done with a folded delay arm including a dispersion-introducing optic and a mirror, and the collecting uses a long-pass filter with a first of the detectors and a short-pass filter with at least a second of the detectors.

30. The method of claim 23, further comprising automatically moving a mirror relative to the security screening structure and the scanned specimen between laser pulse emission iterations, in order to vary directions of subsequent emitted pulses.

* * * * *